(12) United States Patent
Deng et al.

(10) Patent No.: US 8,227,468 B2
(45) Date of Patent: Jul. 24, 2012

(54) CATHEPSIN S INHIBITOR COMPOUNDS

(75) Inventors: Gary G. Deng, Lebanon, IN (US); Konstantinos Gavardinas, Monrovia, IN (US); Prabhakar Kondaji Jadhav, Zioinsville, IN (US); Euibong Jemes Kim, Fishers, IN (US); Matthew Allen Schiffler, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/273,302

(22) Filed: Oct. 14, 2011

(65) Prior Publication Data

US 2012/0095020 A1  Apr. 19, 2012

Related U.S. Application Data

(60) Provisional application No. 61/394,424, filed on Oct. 19, 2010.

(51) Int. Cl.
*A61K 31/496* (2006.01)
*C07D 305/08* (2006.01)
*C07D 407/12* (2006.01)

(52) U.S. Cl. .............. 514/252.13; 514/254.11

(58) Field of Classification Search .................. None
See application file for complete search history.

(56) References Cited

FOREIGN PATENT DOCUMENTS

| WO | 99/14212 A1 | 3/1999 |
|---|---|---|
| WO | 02/40462 A2 | 5/2002 |
| WO | 02/42278 A2 | 5/2002 |
| WO | 2005/039496 A2 | 5/2005 |
| WO | 2008/130322 A1 | 10/2008 |

OTHER PUBLICATIONS

Riese, et al., Regulation of CD1 Function and NK1.1 T Cell Selection and Maturation by Cathepsin, Immunity, vol. 15, 909-919 (2001).
Sukhova, et al., Expression of the Elastolytic Cathepsins S and K in Human Atheroma and Regulation of their Production in Smooth Muscle Cells, J. Clin. Invest., vol. 102(3) 576-583 (1998).
Wiener, et al., Recent Advances in the Design of Cathepsin S Inhibitors, Current Topics in Medicinal Chemistry, vol. 10, 717-732 (2010).
Abdul-Hussien, et al., Collagen Degradation in the Abdominal Aneurysm (A Conspiracy of Matrix Metalloproteinase and Cysteine Collagenases) The American J. of Pathology. vol. 170(3), 809-817 (2007).
Sukhova, et al., Deficiency of cathepsin S reduces atherosclerosis in LDL receptor-deficient mice, The J. of Clinical Investigation vol. 111(6), 897-906 (2003).
Sukhova, et al., Do Cathepsins Play a Role in Abdominal Aortic Aneurysm Pathogenesis? Ann. N.Y. Acad. Sco. 1085:161-169 (2006).
Rodgers, et al., Destabilizing Role of Cathepsin S in Murine Atherosclerotic Plaques, Arterioscler Thromb Vasc Biol., 851-856 (2006).
Nooijer, et al., Leukocyte Cathepsin S is a Potent Regulator of Both Cell and Matrix Turnover in Advanced Atherosclerosis, Arterioscler Thromb Vasc Biol., vol. 29, 188-194 (2009).
Tully, et al., Arylaminoethyl carbamates as a novel series of potent and selective cathepsin S inhibitors, Bioorganic & Medicinal Chemistry Letters, vol. 16, No. 19, Oct. 1, 2006, pp. 5107-5111.
Gustin, et al., Discovery and SAR studies of a novel series of noncovalent cathepsin S inhibitors, Bioorganic & Medicinal Chemistry Letters, vol. 15, No. 6, Mar. 15, 2005, pp. 1687-1691.

*Primary Examiner* — Emily Bernhardt
(74) *Attorney, Agent, or Firm* — R. Craig Tucker

(57) ABSTRACT

The present invention provides a compound of Formula (I):

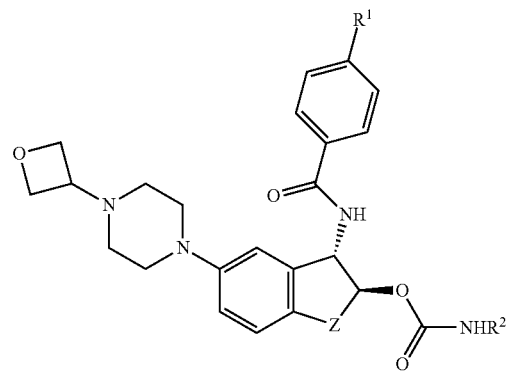

or a pharmaceutically acceptable salt thereof. Also, the present invention provides a pharmaceutical composition comprising a compound of Formula (I) or a pharmaceutically acceptable salt thereof with a pharmaceutically acceptable diluent or carrier. The present invention further provides methods for treating abdominal aortic aneurysm, plaque instability, atherosclerosis, or autoimmune disorders such as rheumatoid arthritis, psoriasis, and lupus comprising administering a therapeutically effective amount of a compound of Formula (I) or a pharmaceutically acceptable salt thereof or a pharmaceutical composition comprising a compound of Formula (I) or pharmaceutically acceptable salt thereof and a pharmaceutically acceptable diluent or carrier.

20 Claims, No Drawings

CATHEPSIN S INHIBITOR COMPOUNDS

This U.S. regular application claims priority under 35 U.S.C. 119(e) to U.S. provisional application Ser. No. 61/394,424, filed 19 Oct. 2010.

The present invention is directed toward inhibitor compounds of the proteolytic enzyme cathepsin S and methods of treatment comprising administration thereof. Specifically, the present invention is directed toward stereoisomers. More specifically, the present invention provides potent, selective and reversible stereoisomer inhibitor compounds having two chiral centers.

Cathepsin S is a lysosomal cysteine protease. It belongs to a larger family of cathepsins, including L, B, K, V and F. Selectivity to cathepsin S may avoid undesired consequences such as side effects. Cathepsin S is produced by inflammatory cells such as dendritic cells, B lymphocytes and macrophages. It is involved in the pathology of several conditions including atherosclerosis and abdominal aortic aneurysm (AAA) (*J. Clin. Invest.* 1999, 104(9), 1191-1197)(*Am. J. Path.* 2007, 170(3), 809-817).

The endothelial cells of the arterial wall may malfunction due to several factors that lead to plaque formation and buildup in the arterial wall including high levels of cholesterol, stress, overall health and genetics. This malfunction leads to the production and recruitment of inflammation cells from the blood that penetrate the arterial wall to protect from damage. These inflammation cells ultimately produce cathepsin S. An effect of cathepsin S is to degrade the extracellular matrix proteins such as elastin and collagen that make up the arterial wall. Although extracellular remodeling of the cells is ongoing to repair the damaged arterial wall, if too much proteolytic degradation of the matrix occurs, compared to deposition of matrix proteins, an imbalance may lead to instability of plaques formed within the arterial wall. Too much plaque instability could result in plaque rupture and potentially thrombotic-related events. Thus, inhibition of cathepsin S provides a means for treating atherosclerosis.

Occasionally, the extracellular matrix of the abdominal aorta may also be weakened by the excess degradation leading to a condition known as AAA. Currently, AAA is the tenth leading cause of death in men greater than 55 years old. There is no known approved medication treatment indicated for AAA. Inhibition of cathepsin S provides an option for addressing this unmet medical need.

Furthermore, Cathepsin S is implicated in autoimmune disorders which may include rheumatoid arthritis, lupus and psoriasis, through its intracellular trafficking involvement in the initiation of an immune response (*Immunity*, 2001, 15, 909-919)(*Eur. J. Immunol.* 2005, 35, 2552-2562). Specifically, cathepsin S cleaves Iip10 (p10) in B lymphocyte and dendritic cells to generate CLIP (class-II associated Ii-peptide). This allows loading of a peptide fragment, e.g., self-antigen, and subsequent presentation of the class II Major Histocompatability Complex (MHC) molecules on the cell surface of the antigen presenting cells. Subsequent activation of immature T cells results thereby generating an autoimmune response. Thus, inhibition of cathepsin S blocks p10 processing and surface presentation of T cell antigens, thereby providing a means for treating autoimmune related disorders such as rheumatoid arthritis, psoriasis, and lupus.

Accordingly the present invention provides a compound of Formula (I):

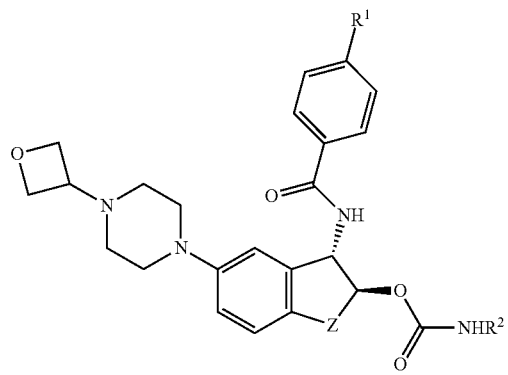

wherein Z is —$CH_2$—, —$CH_2CH_2$—, —$OCH_2$—, —$CH_2CH_2CH_2$—, or —$OCH_2CH_2$—;
$R^1$ is H, F, or Cl;
$R^2$ is H, methyl, ethyl, propyl, or isopropyl;
or a pharmaceutically acceptable salt thereof.

An aspect of the present invention provides a pharmaceutical composition comprising a compound of Formula (I) or a pharmaceutically acceptable salt thereof and a pharmaceutically acceptable diluent or carrier.

Another aspect of the present invention provides methods for treatment of AAA by administering a therapeutically effective amount of a compound or pharmaceutically acceptable salt thereof of the present invention or a pharmaceutical composition comprising a compound or pharmaceutically acceptable salt thereof of the present invention. A further aspect of the present invention provides methods for treatment of AAA in a mammal such as a human, dog, cat, cow, horse, sheep, or monkey by administering a therapeutically effective amount of a compound or pharmaceutically acceptable salt thereof of the present invention or a pharmaceutical composition comprising a compound or pharmaceutically acceptable salt thereof of the present invention. A further aspect of the present invention provides methods for treatment of AAA in a human whose aortic diameter is greater than the normal diameter of approximately 3 cm but less than approximately 5 cm and surgical or endovascular repair is not required, by administering a therapeutically effective amount of a compound or pharmaceutically acceptable salt thereof of the present invention or a pharmaceutical composition comprising a compound or pharmaceutically acceptable salt thereof of the present invention. Yet a further aspect of the present invention provides methods for treatment of AAA in a human whose aortic diameter is greater than approximately 5 cm but surgical or endovascular repair is not a treatment option by administering a therapeutically effective amount of a compound or pharmaceutically acceptable salt thereof of the present invention or a pharmaceutical composition comprising a compound or pharmaceutically acceptable salt thereof of the present invention.

Another aspect of the present invention provides methods for treatment of plaque instability in a mammal such as a human, dog, cat, cow, horse, sheep, or monkey by administering a therapeutically effective amount of a compound or pharmaceutically acceptable salt thereof of the present invention or a pharmaceutical composition comprising a compound or pharmaceutically acceptable salt thereof of the present invention.

A further aspect of the present invention provides methods for treatment of atherosclerosis in a mammal such as a human, dog, cat, cow, horse, sheep, or monkey by administering a therapeutically effective amount of a compound or pharmaceutically acceptable salt thereof of the present invention or a pharmaceutical composition comprising a compound or pharmaceutically acceptable salt thereof of the present invention.

Yet another aspect of the present invention provides methods for treatment of autoimmune disorders in a mammal such as a human, dog, cat, cow, horse, sheep, or monkey in need thereof by administering a therapeutically effective amount of a compound or pharmaceutically acceptable salt thereof of the present invention or a pharmaceutical composition comprising a compound or pharmaceutically acceptable salt thereof of the present invention. A further aspect of the present invention provides methods for treatment of psoriasis, rheumatoid arthritis, or lupus in a human by administering a therapeutically effective amount of a compound or pharmaceutically acceptable salt thereof of the present invention or a pharmaceutical composition comprising a compound or pharmaceutically acceptable salt thereof of the present invention.

A further aspect of the present invention provides a compound or pharmaceutically acceptable salt thereof for use in therapy. Another aspect of the present invention provides a compound or pharmaceutically acceptable salt thereof for use in the treatment of abdominal aortic aneurysm, plaque instability, atherosclerosis, or autoimmune disorders such as rheumatoid arthritis, psoriasis, and lupus. Yet another aspect of the present invention is the use of a compound or pharmaceutically acceptable thereof for the manufacture of a medicament for the treatment of abdominal aortic aneurysm, plaque instability, atherosclerosis, or autoimmune disorders such as rheumatoid arthritis, psoriasis, and lupus.

Another aspect of the present invention provides a pharmaceutical composition comprising a compound or pharmaceutically acceptable salt thereof of the present invention in combination with one or more pharmaceutically acceptable carriers, diluents, or excipients, and optionally one or more other therapeutic agents.

Yet another aspect of the present invention provides a compound of the present invention, or a pharmaceutically acceptable salt thereof, for use in the treatment of abdominal aortic aneurysm, plaque instability, atherosclerosis, rheumatoid arthritis, psoriasis, and lupus.

Yet another aspect of the present invention provides the use of a compound of the present invention, or a pharmaceutically acceptable salt thereof, for the manufacture of a medicament for the treatment of abdominal aortic aneurysm, plaque instability, atherosclerosis, rheumatoid arthritis, psoriasis, and lupus.

Embodiments of the inhibitor compounds and methods for treatment comprising administration thereof in the present invention include any combination of $R_1$, $R_2$ and Z as described above. Specifically, an embodiment of the present invention is directed toward a compound of Formula (I) or pharmaceutically acceptable salt thereof where $R_1$ is H or F. More specifically, an embodiment of the present invention is directed toward a compound of Formula (I) or pharmaceutically acceptable salt thereof where $R_1$ is F.

Another embodiment of the present invention is a compound of Formula (I) or pharmaceutically acceptable salt thereof where $R_2$ is methyl or ethyl. Specifically, an embodiment of the present invention is a compound of Formula (I) or pharmaceutically acceptable salt thereof where $R_2$ is methyl.

Yet another embodiment of the present invention is directed to a compound of Formula (I) or a pharmaceutically acceptable salt thereof where Z is —$CH_2$—, —$CH_2CH_2$—, —$OCH_2$—, —$CH_2CH_2CH_2$—, or —$OCH_2CH_2$—. Specifically, an embodiment of the present invention is a compound of Formula (I) or pharmaceutically acceptable salt thereof where Z is —$CH_2CH_2$— or —$OCH_2$—. Further embodiments of the present invention consist of a combination where $R_1$ is H or F, $R_2$ is methyl or ethyl, and Z is —$CH_2CH_2$— or —$OCH_2$—.

Preferred compounds of the present invention as exemplified hereafter are:
[(3R,4S)-4-[(4-Fluorobenzoyl)amino]-6-[4-(oxetan-3-yl) piperazin-1-yl]chroman-3-yl]N-methylcarbamate,
[(1S,2S)-1-[(4-Fluorobenzoyl)amino]-7-[4-(oxetan-3-yl) piperazin-1-yl]tetralin-2-yl]N-methylcarbamate,
[(1S,2S)-1-[(4-Fluorobenzoyl)amino]-6-[4-(oxetan-3-yl) piperazin-1-yl]indan-2-yl]N-methylcarbamate,
[(8S,9S)-9-[(4-fluorobenzoyl)amino]-2-[4-(oxetan-3-yl)piperazin-1-yl]-6,7,8,9-tetrahydro-5H-benzo[7]annulen-8-yl]N-methylcarbamate, and
[(4S,5S)-5-[(4-fluorobenzoyl)amino]-7-[4-(oxetan-3-yl)piperazin-1-yl]-2,3,4,5-tetrahydro-1-benzoxepin-4-yl]N-methylcarbamate.

More preferred compounds of the present invention are:
[(3R,4S)-4-[(4-Fluorobenzoyl)amino]-6-[4-(oxetan-3-yl) piperazin-1-yl]chroman-3-yl]N-methylcarbamate,
[(1S,2S)-1-[(4-Fluorobenzoyl)amino]-7-[4-(oxetan-3-yl) piperazin-1-yl]tetralin-2-yl]N-methylcarbamate, and
[(8S,9S)-9-[(4-Fluorobenzoyl)amino]-2-[4-(oxetan-3-yl) piperazin-1-yl]-6,7,8,9-tetrahydro-5H-benzo[7]annulen-8-yl]N-methylcarbamate.

Most preferred compound of the present invention is:
[(3R,4S)-4-[(4-Fluorobenzoyl)amino]-6-[4-(oxetan-3-yl) piperazin-1-yl]chroman-3-yl]N-methylcarbamate.

As used above and throughout the specification of the invention, the following terms, unless otherwise indicated will have the following meaning:

The term "abdominal aortic aneurysm" (or "AAA") as used herein shall mean a localized dilation or bulge of the abdominal aorta in a mammal causing the size of at least a segment of the abdominal aorta to exceed the size of an otherwise considered normal state. The abdominal aorta may be measured and compared in terms of any measurement dimension including but not limited to luminal diameter, luminal perimeter, and luminal area. The means for measurement and diagnosis may be through the use of ultrasound, CT scan, or other imaging techniques. For example, AAA is present in a human when the aortic diameter is greater than its normal diameter, approximately 3 cm. If the aortic diameter is however more than approximately 5 cm, then immediate surgical or endovascular repair (stent or graft) is the standard of care to prevent rupture and potential fatality. If however such treatment is unavailable or not an option due to any reason, e.g., age, then this population may also be treated using the present invention.

The term "in need thereof" as used herein shall mean having or being diagnosed with a condition, e.g., atherosclerosis, AAA, autoimmune disorder such as psoriasis, lupus or rheumatoid arthritis, that requires treatment.

The term "mammal" as used herein shall mean a human or nonhuman mammal such as a dog, cat, cow, horse, sheep, or monkey.

The term "pharmaceutically acceptable salt thereof" refers to salts of the compounds of the present invention. Examples and methods for their preparation are well within the knowledge of those skilled in the art. See, for example, Stahl et al., "Handbook of Pharmaceutical Salts: Properties, Selection and Use," VCHA/Wiley-VCH, 2002.

The term "therapeutically effective amount" refers to the amount or dose of a compound of Formula (I) or composition comprising a compound of Formula (I) to achieve treatment. A therapeutically effective amount can be readily determined by the attending physician, as one skilled in the art, by considering a number of factors known to a person skilled in the art such as, for example, weight, height, age, general health of the patient, severity of the condition, mode of administration, dosing regimen, etc.

The term "treatment" as used herein shall mean slowing the rate or progression of a disease state. It may also include halting the disease state. The term may further include not only halting the disease but also reducing any disease state that already has occurred. For example, in the context of AAA, the term "treatment" may mean slowing of the expansion rate of an abdominal aortic aneurysm. It may also include stopping the expansion of the abdominal aortic aneurysm. Furthermore, it may include reducing any expansion that has already occurred.

The designation "⬛︎" refers to a bond that protrudes forward out of the plane of the page.

The designation "⸾⸾⸾" refers to a bond that protrudes backward out of the plane of the page.

The terms "—OCH$_2$—" and "—OCH$_2$CH$_2$—" within the definition of "Z" are understood to mean that the oxygen is adjacent to the fused benzo ring.

The compounds of the present invention are preferably formulated as pharmaceutical compositions. Examples and methods for their preparation are well within the knowledge of those skilled in the art. See, for example, Remington: The Science and Practice of Pharmacy (A. Gennaro, et al., eds. 19$^{th}$ ed., Mack Publishing Co., 1995).

The compounds of Formula I, or salts thereof, may be prepared by a variety of procedures known in the art, as well as those described in the Schemes, Preparations, and Examples below. The specific synthetic steps for each of the routes described may be combined in different ways to prepare compounds of Formula I, or pharmaceutically acceptable salts thereof.

The following preparations and examples further illustrate the invention and represent typical synthesis of the compounds of Formula (I), including any novel compounds, as described generally above. The reagents and starting materials are readily available to, or may be readily synthesized by, one of ordinary skill in the art. It should be understood that the Preparations and Examples are set forth by way of illustration and not limitation, and that various modifications may be made by one of ordinary skill in the art.

The R or S configuration of compounds of the invention may be determined by standard techniques such as X-ray analysis and correlation with chiral-HPLC retention time. The naming of the following Preparations and Examples is generally done using the IUPAC naming feature in Symyx Isentris® version 3.2.3.

As used herein, the following terms have the meanings indicated: "AcOH" refers to acetic acid; "BCA" refers to bicinchoninic acid; "b.i.d." refers to two times a day; "brine" refers to saturated aqueous NaCl solution; "cat." refers to a catalytic amount; "CD74" refers to the invariant chain (Ii); "CDI" refers to 1,1'-carbonyldiimidazole; "DMAP" refers to 4-dimethylaminopyridine; "DMSO" refers to dimethyl sulfoxide; "DTT" refers to dithiothreitol; "EDTA" refers to ethylenediaminetetraacetic acid; "EtOH" refers to ethanol; "hr." refers to hour(s); "IC$_{50}$" refers to the concentration of an agent which produces 50% of the maximal inhibitory response possible for that agent or, alternatively, to the concentration of an agent which produces 50% displacement of ligand binding to the receptor; "IMAC" refers to Immobilized Metal Affinity Chromatography; "IPA" refers to isopropyl alcohol; "LC ES/MS" refers to liquid chromatography electrospray mass spectrometry; "MCPBA" refers to meta-chloroperoxybenzoic acid; "MeOH" refers to methanol; "min." refers to minute(s); "NBS" refers to N-bromosuccinimide "NMP" refers to N-methylpyrrolidine; "N/A" refers to not available; "p10" refers to a fragment of the invariant chain CD74; "PBS" refers to phosphate buffered saline; "PWBC" refers to peripheral white blood cells; "RFU" refers to relative fluorescence units; "SFC" refers to supercritical fluid chromatography; "STAB" refers to sodium triacetoxyborohydride; "SDS" refers to sodium dodecyl sulfate; "THF" refers to tetrahydrofuran; "t-boc" or "boc" refers to tert-butoxycarbonyl; "TRITON® X-100" refers to polyethylene glycol p-(1,1,3,3-tetramethylbutyl)-phenyl ether.

The substituents, unless otherwise indicated, are as previously defined.

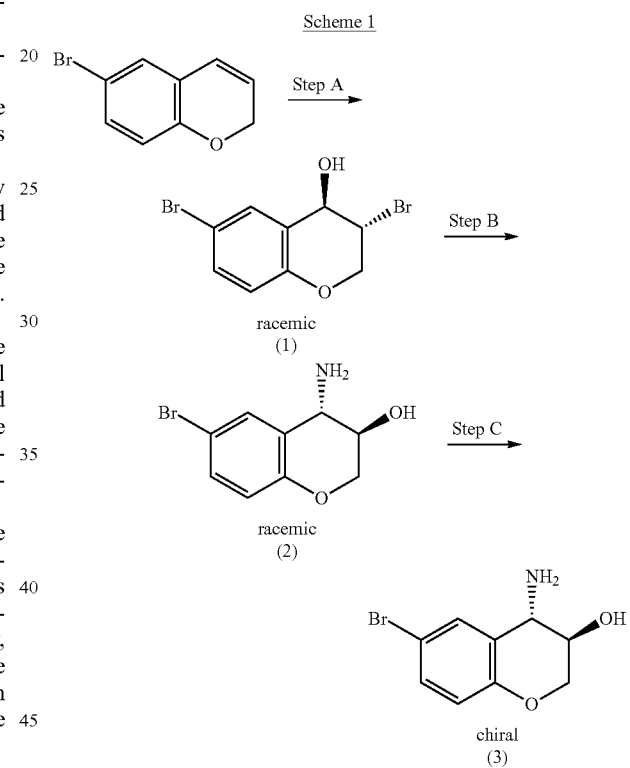

Scheme 1

Formation of intermediate (3) can be carried out in accordance with reactions as depicted in Scheme 1.

In Scheme 1, Step A, 6-bromo-2H-chromene is treated with NBS to form a bromohydrin (1). Preferred conditions use a solvent mixture of DMSO/water at about 0-50° C., but more preferably at room temperature.

In Step B, the bromohydrin (1) is treated with ammonium hydroxide to provide the amino alcohol (2). For example, the bromohydrin is reacted with ammonium hydroxide in a solvent mixture of THF and EtOH at room temperature to 60° C. for 4 to 24 hr.

In Scheme 1, Step C, the racemic amino alcohol is resolved into its 3R, 4S and 3S, 4R enantiomers to provide the chiral amino alcohol (3). Methods for resolution are commonly known to those skilled in the art and include crystallization as a salt of a chiral acid, or separation of the enantiomers by chiral chromatography.

6-Bromo-2H-chromene is commercially available or can be prepared by methods commonly known in the art. For example 6-bromo-4-chromanone can be reduced to the alcohol and subsequently eliminated to obtain 6-bromo-2H-chromene.

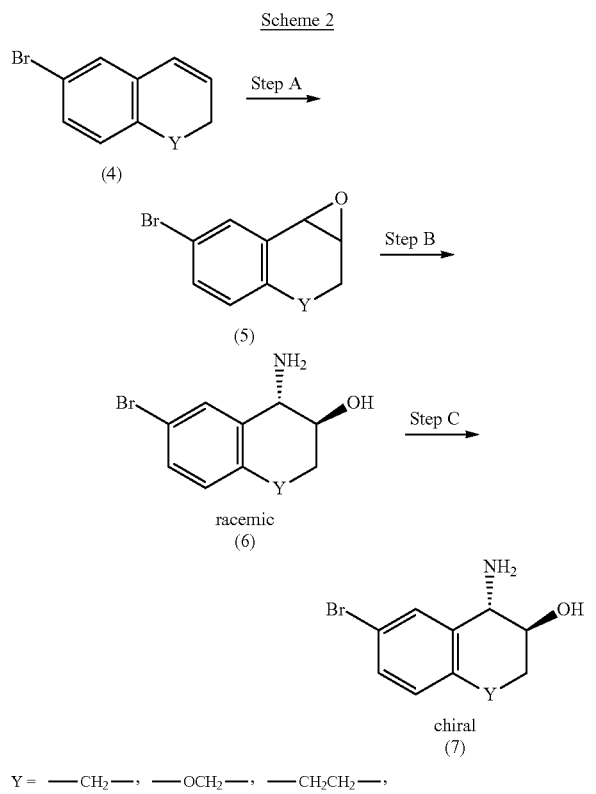

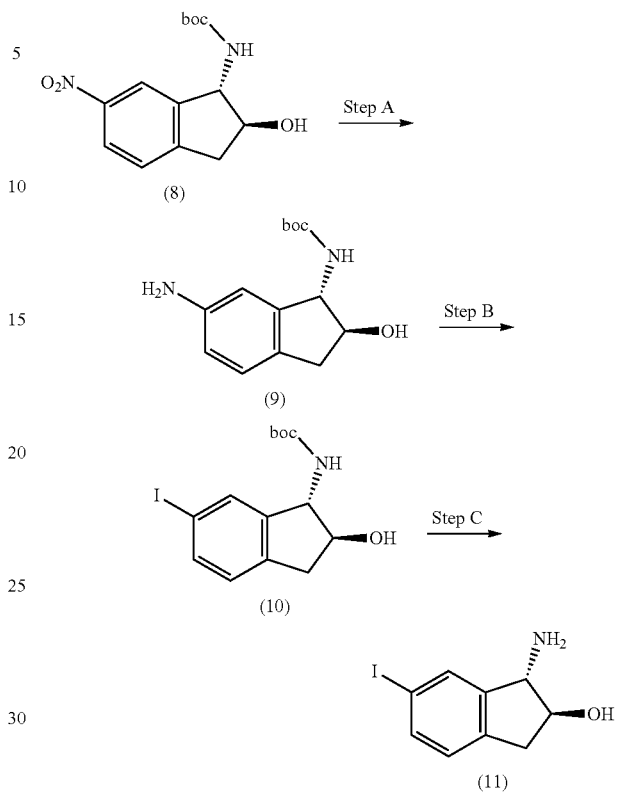

In Scheme 2 is depicted the synthesis for the intermediate of formula (7).

In Scheme 2, Step A, a cyclic alkene of formula (4) is oxidized with MCPBA to obtain an epoxide of formula (5). The reaction is performed in a biphasic mixture of a halogenated solvent, such as dichloromethane and an aqueous base, such as aqueous sodium bicarbonate. The MCPBA is added in portions at −10 to 10° C. and the reaction allowed to warm to room temperature with stirring for 1 to 8 hr. Additional MCPBA is added if needed.

In Step B, an epoxide of formula (5) is treated with ammonia to form a racemic amino alcohol of formula (6). Preferred conditions use a sealed vessel with an inert solvent, such as THF, with the addition of ammonia in MeOH. The reaction is heated at 50 to 100° C. for 1 to 4 days, adding additional ammonia if necessary.

In Scheme 2, Step C a racemic amino alcohol (6) is resolved to a chiral amino alcohol of formula (7) as previously described in Scheme 1, Step C. For example, 1-amino-7-bromo-tetralin-2-ol (Y=—CH$_2$—) is resolved by crystallization with (+)-di-1,4-toluoyl-D-tartaric acid. The free amine can be obtained by treatment of the salt with aqueous base to obtain the (1S,2S)-amino alcohol wherein Y=—CH$_2$—. Alternatively, the racemic material (6) can be carried through to final products and the enantiomers separated by chiral chromatography.

It will be understood by one skilled in the art that the cyclic alkenes of formula (4) can readily be obtained either commercially or by methods known in the literature. For example, the corresponding ketone can be reduced to the alcohol and subsequently eliminated to the alkene.

Formation of intermediate (11) can be carried out in accordance with reactions as depicted in Scheme 3.

In Scheme 3, Step A, the amino indane (9) is obtained from the nitro indane (8) by hydrogenation over 5% palladium on carbon according to procedures contained in the literature for the 1R,2R enantiomer (U.S. Pat. No. 7,326,731 B2).

In Step B, the amino indane (9) is converted to the iodoindane (10) using a Sandmeyer reaction. The diazonium salt is formed in situ in a solvent such as acetonitrile using p-toluenesulfonic acid and an aqueous solution of sodium nitrite. The diazonium salt is subsequently treated with an aqueous solution of potassium iodide at a temperature of 0 to 30° C. for 0.5 to 6 h to provide the iodoindane (10).

In Step C, the boc protected iodoindane (10) is taken to the iodo amino indane (11) under acidic conditions, such as HCl or trifluoroacetic acid. Methods for introducing and removing nitrogen protecting groups are well known in the art (see, e.g., Greene and Wuts, *Protective Groups in Organic Synthesis*, 3$^{rd}$ Ed., John Wiley and Sons, New York, (1999)). Preferred conditions use HCl in dioxane at 0 to 25° C. for 0.5 to 4 h.

Tert-butyl-N-[(1S,2S)-6-amino-2-hydroxy-indan-1-yl] carbamate (8) can be prepared by methods known in the art. For example, racemic-trans-1-amino-6-nitroindan-2-ol can be obtained in six steps from indene (*Adv. Synth. Catal.* 2005, 347, 255-265). The racemic material is resolved and isolated as the 1R,2R and 1S,2S salts of (+)-L-mandelic acid. The 1S,2S salt is freed to 1S,2S-trans-1-amino-6-nitroindan-2-ol and the amine subsequently protected as the tert-butyl carbamate to obtain material in greater than 97% ee as analyzed by chiral HPLC.

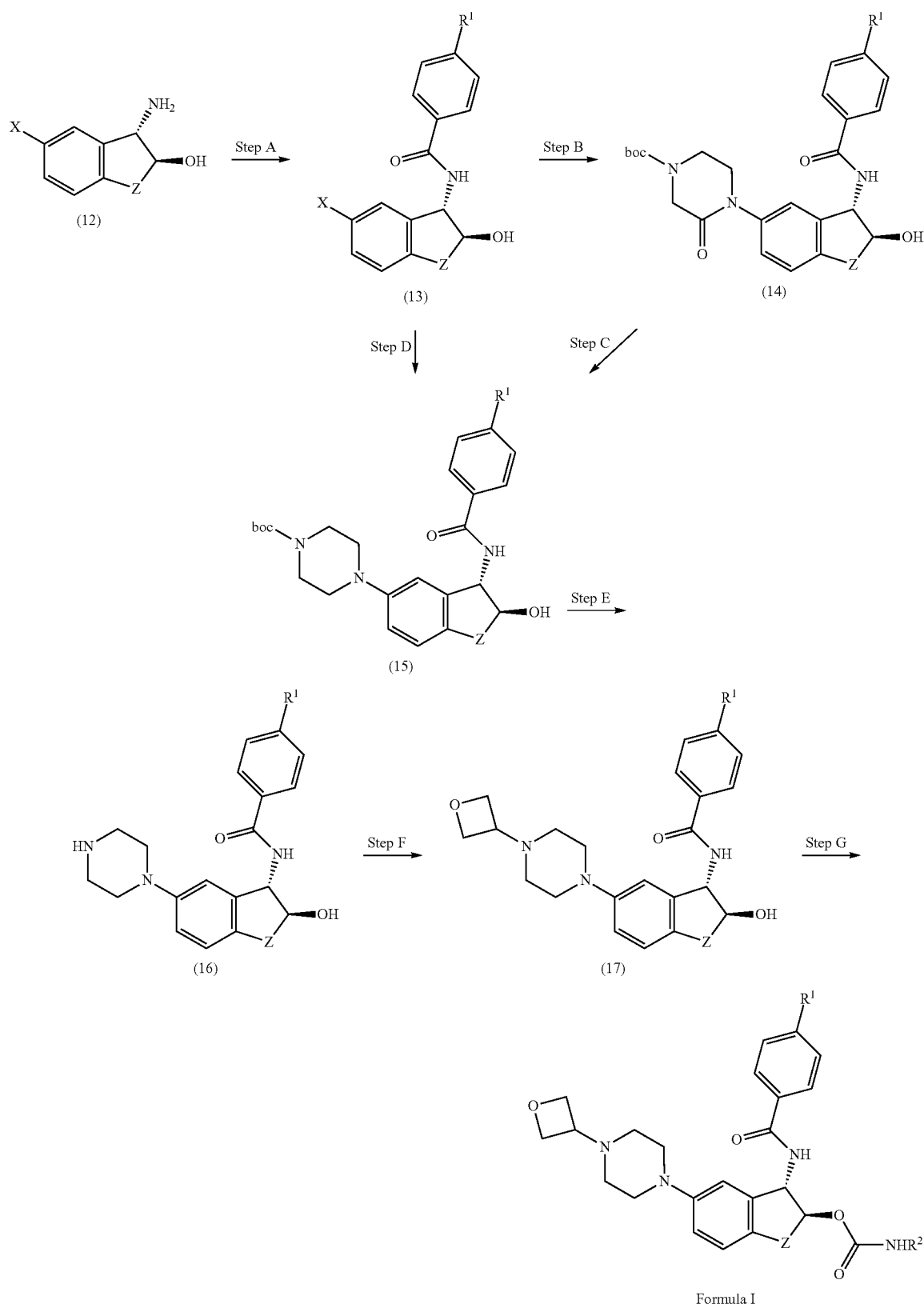
Scheme 4

Formation of compounds of the invention of Formula I can be carried out in accordance with reactions as depicted in Scheme 4.

In Scheme 4, Step A, the amino alcohol of formula (12) (either chiral or racemic) is acylated to obtain an amide of formula (13). Various acylation methods are well known in the art using either a carboxylic acid or an acid chloride. Preferred conditions use an appropriate benzoyl chloride in a solvent mixture of THF and aqueous sodium bicarbonate at a temperature of 0 to 25° C. for 1 to 8 h. If the starting amino alcohol is used as the salt of a chiral acid, sufficient base is used to generate the free amine.

In Step B, the bromo or iodo amide of formula (13) is coupled with a protected t-oxo-piperazine using copper (I) iodide and a ligand, such as sym-dimethylethylene diamine to provide an oxopiperazine of formula (14). The reaction is preferably performed in a sealed vessel, under an inert atmosphere, in the presence of an inorganic base such as potassium carbonate. The reaction is run in an inert solvent, such as NMP at a temperature of 80 to 150° C.

In Scheme 4, Step C, the oxopiperazine is selectively reduced in the presence of the benzamide to provide the piperazine of formula (15). The reaction is accomplished using a reducing agent such as borane-dimethyl sulfide complex in an inert solvent such as THF at a temperature of 0 to 40° C. for one to four hours. Additional borane-dimethyl sulfide complex may be used to drive the reaction to completion.

Alternatively, in Step D, the piperazine is reacted directly with the iodo or bromo amide (13) using N-tert-butoxycarbonylpiperazine in a coupling reaction. The reaction proceeds in the presence of a Pd catalyst, such as allylpalladium(II) chloride dimer and a ligand such as tri-tert-butylphosphonium tetrafluoroborate. A base is used, such as sodium tert-butoxide in an inert solvent such as DMSO at temperature of 20 to 120° C. for 0.5 to 8 hr. to provide the piperazine of formula (15).

In Step E, the boc protecting group is removed to give the unprotected piperazine of formula (16). Acidic conditions for removal of boc groups, such as HCl in dioxane, are well known in the art.

Subsequently, in Step F, the unprotected amine (16) is reacted in a reductive amination with 3-oxetanone to provide an oxetanyl piperazine of formula (17). Various methods for accomplishing reductive aminations are well known in the art. Preferred conditions use a reducing agent, such as sodium triacetoxy borohydride, in an inert solvent such as acetonitrile. The reaction is carried out at 0 to 40° C. for about 0.5 to 4 hr. Additional sodium triacetoxy borohydride and 3-oxetanone may be added to drive the reaction to completion. Alternatively, the reaction can be accomplished using a reducing agent such as sodium cyanoborohydride, in a solvent mixture such as MeOH and glacial acetic acid, in the presence of molecular sieves. The reaction proceeds at a temperature of 0 to 60° C. for about 1 to 24 hr.

In Scheme 4, Step G, the alcohol of the oxetanyl piperazine (17) is converted to the carbamate of Formula I. There are various means available to the skilled artisan for synthesizing carbamates such as triphosgene/amine, 4-nitrophenyl chloroformate/amine, CDI/amine or directly with an appropriately substituted isocyanate. The preferred method for compounds of the invention wherein Z=—CH$_2$—, makes use of the appropriate isocyanate (O=C=N—R$^2$). For example, the alcohol (17) in an aprotic solvent such as dichloromethane, dioxane, or preferably THF, in the presence of an organic base, such as DMAP or preferably 4-pyrrolidinopyridine, is treated with methyl isocyanate. The reaction is run in a sealed vessel at 20 to 70° C. for about 2 to 16 hr. Compounds of the invention wherein the carbamate moiety is a primary carbamate (R$^2$=H) can be synthesized using CDI/ammonia, sodium cyanate, or chlorosulfonyl isocyanate. Other methods make use of trichloroacetyl isocyanate in an aprotic solvent. Subsequently, the trichloroacetyl group is cleaved using neutral Al$_2$O$_3$ or an organic acid such as p-toluene sulfonic acid. A preferred method for synthesis of the carbamate of Formula I makes use of CDI in an inert solvent such as THF at 0 to 25° C. for 4-20 hr. to form the imidazole N-carboxylic ester in situ. Subsequent reaction with an appropriate amine (H$_2$NR$^2$) provides the carbamate of Formula I.

It will be recognized by one skilled in the art that the intermediates described above can be carried along as racemic mixtures and resolved as a final step, preferably by chiral HPLC, to provide enantiomerically pure compound.

PREPARATION 1

6-Bromochroman-4-ol

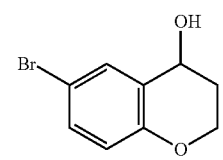

To a suspension of 7-bromo-3,4-dihydronaphthalen-1(2H)-one (3.95 kg, 17.4 mol) in ethanol (20 L) at room temperature add sodium borohydride (221 g, 5.84 mol) in portions over 3 hr. Concentrate the clear red solution. Add the residue into ice (about 3 kg) to form a suspension and then slowly add ice-cooled 0.5 M HCl (10 L) into the above suspension with stirring. Extract the mixture with methyl tert-butyl ether (20 L and 5 L). Wash the combined organic phase with saturated aqueous sodium bicarbonate (10 L) and brine (2×10 L), concentrate the solvent under reduced pressure and dry the wet solid in air overnight to obtain the title compound as a pale yellow solid (4.10 kg, quantitative). LC-ES/MS m/z 211 [M−H−2O+H]+.

Prepare the alcohols in the table below by essentially following the procedure described in Preparation 1 using the appropriate ketone.

| Prep | Chemical name | Structure | LC-ES/MS m/z ($^{79}$Br/$^{81}$Br) |
|---|---|---|---|
| 2 | 7-Bromotetralin-1-ol | 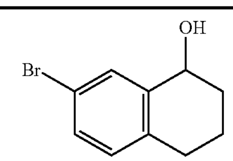 | 209/211 [M−H$_2$O + H]$^+$ |
| 3 | 2-Bromo-6,7,8,9-tetrahydro-5H-benzo[7]annulen-9-ol | 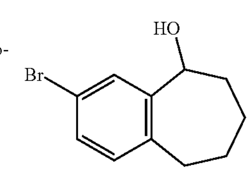 | GC/MS 222/224 [M+] |

PREPARATION 9

Racemic-trans-3,6-dibromochroman-4-ol

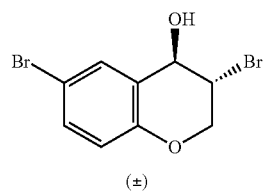

(±)

To a solution of DMSO (16 L) and water (2.5 L) at room temperature add 6-bromo-2H-chromene (4.90 kg, 23.2 mol). Add NBS (3.47 kg, 19.5 mol) in portions over 3.5 hr. Pour the mixture into methyl tert-butyl ether (12 L) and water (18 L), separate the two layers. Wash the organic layer with saturated sodium bicarbonate (7 L), water (8 L) and brine (2×8 L). Back extract the aqueous layer with methyl tert-butyl ether (4 L) and evaporate the solvent of the combined organic layers under reduced pressure to obtain the title compound as a reddish brown solid (5.10 kg, 71%).

PREPARATION 10

(3R,4S)-4-Amino-6-bromo-chroman-3-ol

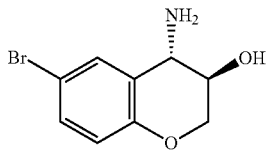

To a solution of racemic-trans-3,6-dibromochroman-4-ol (5.10 kg, 16.6 mol) in tetrahydrofuran (5.0 L) and ethanol (5.0 L) at room temperature, add ammonium hydroxide (13.0 L) in one portion and slowly heat to 43° C. over 2 hr. and continue heating for 14 hr. Concentrate the mixture under reduced pressure to remove about 9 L of solvent. Add methyl tert-butyl ether (10 L) to the residual slurry and stir the mixture for 3 hr. at 25° C. Collect the precipitate by filtration, wash with water (2×2 L) and then methyl tert-butyl ether (3×1.5 L) to obtain a wet solid. Dry in air at room temperature overnight to obtain the title compound as a pale yellow solid (2.78 kg, 69%). LC-ES/MS m/z ($^{79}$Br) 244 [M+H]$^+$. Separate the enantiomers by purifying in 100 g portions on a 11×33 cm CHIRALPAK® AD, 20 μm column eluting with 100% methanol with 0.2% dimethylethylamine (steady state recycle purification) to obtain the 3S,4R enantiomer (isomer 1, 1362.5 g, 97.4% ee) and the title compound (isomer 2, 1323.7 g, 97.5% ee). Conditions for analytical chiral HPLC analysis: 4.6×150 mm CHIRALPAK® AD-H 5 μm column, 100% methanol with 0.2% dimethylethylamine, flow rate 0.5 mL/min., isomer 1 $T_R$=4.69 min, isomer 2 $T_R$=6.27 min.

---

| Prep | Chemical name | Structure | LC-ES/MS m/z ($^{79}$Br/$^{81}$Br) |
|---|---|---|---|
| 4 | 7-Bromo-2,3,4,5-tetrahydro-1-benzoxepin-5-ol | 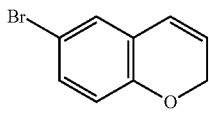 | 265/267 [M + Na]$^+$ |

PREPARATION 5

6-Bromo-2H-chromene

To a solution of 6-bromochroman-4-ol (3.98 kg, 17.4 mol) in toluene (18 L) add p-toluenesulfonic acid monohydrate (95 g, 499.42 mmol) at room temperature. Attach a Dean-Stark trap and reflux for 3 hr. and 50 min. Allow the mixture to cool to 50° C. in air and pour into saturated aqueous sodium bicarbonate (10 L) and ice (about 3 kg) with stirring. Separate the two layers. Back extract the aqueous layer with methyl tert-butyl ether (4 L). Wash the organic layer with saturated sodium bicarbonate (10 L) and brine (1×10 L), and evaporate the solvent under reduced pressure to obtain the title compound as a brown oil (4.90 kg, >100%, contains toluene). LCMS m/z ($^{79}$Br) 209 [M+H]$^+$.

Prepare the alkenes in the table below by essentially following the procedure described in Preparation 5 using the appropriate alcohol.

| Prep | Chemical name | Structure | GC/MS m/z ($^{79}$Br/$^{81}$Br) |
|---|---|---|---|
| 6 | 6-Bromo-1,2-dihydronaphthalene | 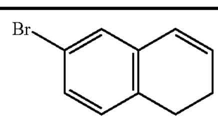 | 208/210 [M+] |
| 7 | 2-Bromo-6,7-dihydro-5H-benzo[7]annulene | 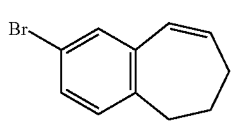 | 222/224 [M+] |
| 8 | 7-Bromo-2,3-dihydro-1-benzoxepine | 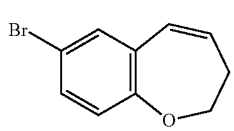 | N/A |

PREPARATION 11

Racemic-cis-6-bromo-1a,2,3,7b-tetrahydronaphtho[1,2-b]oxirene

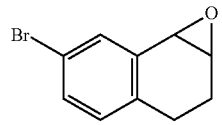

To a solution of 6-bromo-1,2-dihydronaphthalene (250 g, 1.20 mol) in dichloromethane (3.75 L) add saturated aqueous sodium bicarbonate (1250 mL) and cool to 0-5° C. Add MCPBA (77%, 275 g, 1.23 mol, 1.03 eq) in portions. Stir the mixture mechanically at 0-5° C. for 1.5 hr. and allow to warm to room temperature. Stir at room temperature for approximately 1.5 hr. and add additional MCPBA (77%, 15.0 g, 67 mmol, 0.05 eq) at room temperature and stir for approximately one hour. Dilute the mixture with dichloromethane (3750 mL) and separate the layers. Wash the organic layer with saturated aqueous sodium bicarbonate (3 L). Mix a 10% aqueous sodium bisulfate solution (3750 mL) with aqueous saturated sodium bicarbonate (1250 mL) to prepare a solution with a final pH of approximately 7. Add this solution to the dichloromethane layer and stir at room temperature for about 10 min. Separate the layers, wash the organic layer with saturated aqueous sodium bicarbonate (3 L) and brine (3 L). Concentrate in vacuo to obtain the title compound as an oil (263 g, 98%). GC/MS m/z ($^{79}$Br/$^{81}$Br) 224/226 [M+].

Prepare the epoxides in the table below by essentially following the procedure described in Preparation 11 using the appropriate alkene.

| Prep | Chemical name | Structure | GC/MS m/z ($^{79}$Br/$^{81}$Br) |
|---|---|---|---|
| 12 | 2-Bromo-6,7-dihydro-5H-benzo[7]annulene oxide | 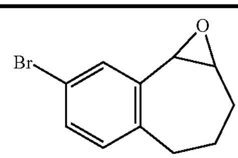 | 238/240 [M+] |
| 13 | 7-Bromo-2,3-dihydro-1-benzoxepine oxide | 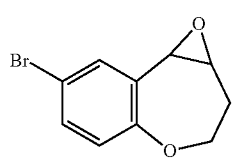 | LC-ES/MS m/z ($^{79}$Br/$^{81}$Br) 241/243 [M + H]+ |

PREPARATION 14

Racemic-trans-1-amino-7-bromo-tetralin-2-ol

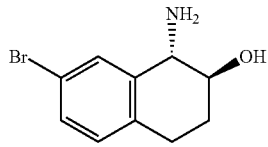

In a 2 L pressure reactor that is equipped with a mechanical stirrer dissolve racemic-cis-6-bromo-1a,2,3,7b-tetrahydronaphtho[1,2-b]oxirene (67.0 g, 298 mmol) in tetrahydrofuran (200 mL). Add 7 M ammonia in methanol (350 mL), seal the reactor and stir at 70° C. for 2 days. Add additional 7 M ammonia in methanol (140 mL), seal the reactor and stir at 70° C. for 1 day. Concentrate the reaction slurry in vacuo to obtain a residue (68.1 g). Add diethyl ether (760 mL) and stir the slurry at room temperature for approximately 5 hr. Collect the solid by filtration, rinse with diethyl ether (2×215 mL) and dry overnight to obtain the title compound (58.1 g, 81%). GC/MS m/z ($^{79}$Br/$^{81}$Br) 224/226 [M−NH$_2$]+.

Prepare the aminoalcohols in the table below by essentially following the procedure described in Preparation 14 using the appropriate epoxide.

| Prep | Chemical name | Structure | LC-ES/MS m/z ($^{79}$Br/$^{81}$Br) |
|---|---|---|---|
| 15 | Racemic-trans-5-amino-3-bromo-6,7,8,9-tetrahydro-5H-benzo[7]annulen-6-ol | 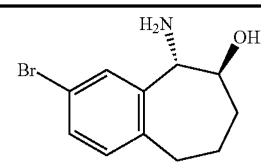 | 256/258 [M + H]+ |
| 16 | Racemic-trans-5-amino-7-bromo-2,3,4,5-tetrahydro-1-benzoxepin-4-ol | 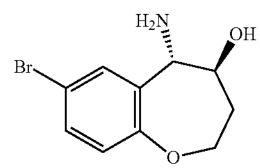 | 258/260 [M + H]+ |

PREPARATION 17

(1S,2S)-1-Amino-7-bromo-1,2,3,4-tetrahydronaphthalen-2-ol (2S,3S)-2,3-bis(4-methylbenzoyloxy)succinate

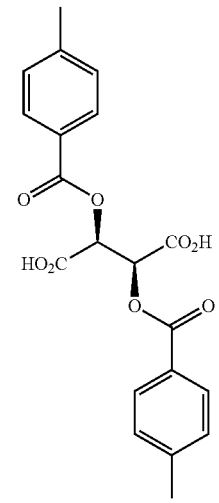

Add (+)-di-1,4-toluoyl-D-tartaric acid (2.30 kg, 5.95 mol) in one portion to a solution of racemic-trans-1-amino-7-bromo-1,2,3,4-tetrahydronaphthalen-2-ol (1.40 kg, 5.78 mol) in acetonitrile (16.0 L) and water (3.50 L). Heat the thick suspension to reflux (77° C.) under nitrogen for 30 min. The stirrer does not start to stir until about 46° C. Turn off the heat to the oil bath and allow the mixture to cool to room temperature with stirring. After 5 hr., filter the thick slurry through a Büchner funnel and rinse with acetonitrile (2 L). Continue to filter for one hour until no more solvent is collected. Dry the wet cake in air at room temperature overnight to obtain the desired salt as a yellow solid (1.70 kg). Add the solid into acetonitrile (15 L) and water (3.3 L) and heat the resulting thick slurry to reflux (77° C.) under nitrogen with stirring for 30 min. Turn off the heat to the oil bath and allow to cool to room temperature with stirring. After 5 hr., filter the thick slurry through a Büchner funnel and rinse with acetonitrile (2 L). Continue to filter for 30 min. until no more solvent is collected. Dry the wet cake at room temperature for 48 h to obtain the desired salt as a pale yellow solid (800 g, 22%). LC-ES/MS m/z ($^{79}$Br) 242 [M+H]$^+$ for the free base. 99.0% ee. Analytical conditions for enantiomeric excess determination by supercritical fluid chromatography (SFC): Column: CHIRALPAK® AD-H (0.46×250 mm, 5 μm), carbon dioxide flow rate: 2.55 mL/min., co-solvent: methanol with 0.1% diethyl amine, co-solvent flow rate: 0.45 mL/min., back pressure: 150 bar, column temperature: 40.9° C. Isomer 1 $T_R$=7.36 min, 0.5% area and isomer 2 (title compound) $T_R$=8.46 min., 99.5% area.

PREPARATION 18 tert-Butyl N-[(1S,2S)-6-amino-2-hydroxy-indan-1-yl]carbamate

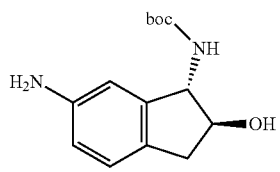

Obtain tert-butyl N-[(1S,2S)-2-hydroxy-6-nitro-indan-1-yl]carbamate of >97% ee by essentially following literature procedures (Kozhushkov, S. I. et. al. *Adv. Synth. Catal.* 2005, 347, 255-265). Reduce the nitro group using the same procedure as described for the 1R, 2R enantiomer (U.S. Pat. No. 7,326,731 B2) to obtain the title compound.

PREPARATION 19 tert-Butyl N-[(1S,2S)-2-hydroxy-6-iodo-indan-1-yl]carbamate

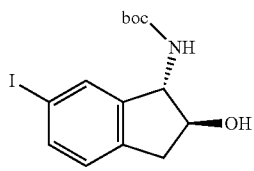

Cool a suspension of tert-butyl N-[(1S,2S)-6-amino-2-hydroxy-indan-1-yl]carbamate (25.0 g, 94.6 mmol) in acetonitrile (800 mL) in an ice bath for 30 min and add p-toluenesulfonic acid monohydrate (53.97 g, 283.7 mmol) in one portion. Add a solution of sodium nitrite (13.05 g, 189.2 mmol) in water (30 mL) to the mixture in portions for 5 min and stir for 30 min. Add a solution of potassium iodide (39.25 g, 236.5 mmol) in water (50 mL) dropwise to the mixture over 10 min. and stir for 20 min. in an ice bath. Allow the mixture to warm up to room temperature and stir for 1.5 hr. Make the dark red solution alkaline with 10% aqueous sodium carbonate. Concentrate the resulting mixture in vacuo to remove the acetonitrile. Collect the brown precipitate by filtration and dry in a vacuum oven at 50° C. overnight to obtain the title compound (33.9 g, 96%). LC-ES/MS m/z 320 [M+H]$^+$.

PREPARATION 20

N-[(3R,4S)-6-Bromo-3-hydroxy-chroman-4-yl]-4-fluoro-benzamide

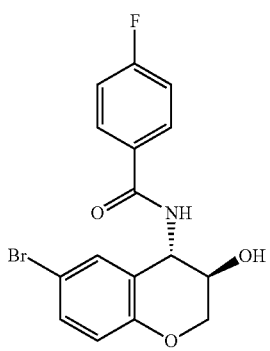

To a suspension of (3R,4S)-4-amino-6-bromo-chroman-3-ol (692 g, 2.84) and sodium bicarbonate (476 g, 5.67 mol) in tetrahydrofuran (3.0 L) and water (3.0 L) at 17° C. add 4-fluorobenzoyl chloride (369 mL, 3.12 mol) dropwise via addition funnel over 15 min. and stir for 2 hr. Add water (2 L) and methyl tert-butyl ether (3.5 L) and stir for 5 min. Separate the organic phase and wash it with water (2 L) and brine (2 L). Dry the organic portion over anhydrous magnesium sulfate and concentrate in vacuo to obtain a pale yellow solid (2.3 kg). Triturate the solid in heptane (5 L) at 25° C. for 3 h. Collect by filtration and dry in an oven at 50° C. for 12 hr. to obtain the title compound (975 g, 94%) as a white solid. LC-ES/MS m/z ($^{79}$Br/$^{81}$Br) 366/368 [M+H]$^+$.

Prepare the amides in the table below by essentially following the procedure described in Preparation 20 using the appropriate racemic or enantiopure aminoalcohol free base or salt. When using the salt of the aminoalcohol (Preparation 21) use saturated sodium bicarbonate as the base.

| Prep | Chemical name | Structure | LC-ES/MS m/z ($^{79}$Br/$^{81}$Br) |
|---|---|---|---|
| 21 | N-[(1S,2S)-7-Bromo-2-hydroxy-tetralin-1-yl]-4-fluoro-benzamide | 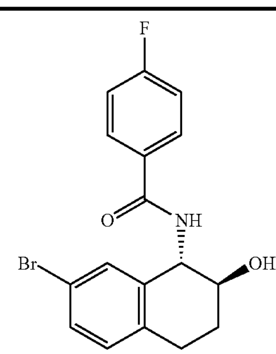 | 362/364 [M + H]$^+$ |

-continued

| Prep | Chemical name | Structure | LC-ES/MS m/z ($^{79}$Br/$^{81}$Br) |
|---|---|---|---|
| 22 | Racemic-trans-N-[2-bromo-8-hydroxy-6,7,8,9-tetrahydro-5H-benzo[7]annulen-9-yl]-4-fluoro-benzamide | 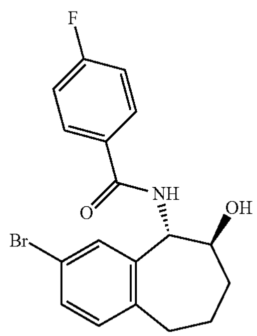 | 376/378 [M + H]$^+$ |
| 23 | Racemic-trans-N-[7-bromo-4-hydroxy-2,3,4,5-tetrahydro-1-benzoxepin-5-yl]-4-fluoro-benzamide | 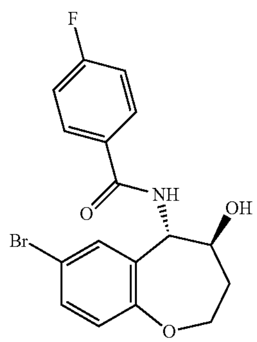 | 380/382 [M + H]$^+$ |

PREPARATION 24

4-Fluoro-N-[(1S,2S)-2-hydroxy-6-iodo-indan-1-yl]benzamide

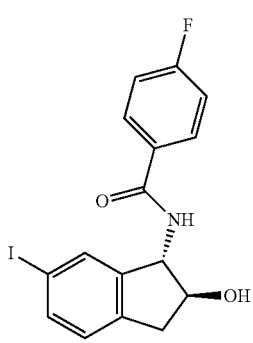

To a solution of tert-butyl N-[(1S,2S)-2-hydroxy-6-iodo-indan-1-yl]carbamate (39.6 mmol, 14.9 g) in 1,4-dioxane (200 mL), add a solution of 4 M hydrogen chloride in dioxane (100 mL) at room temperature and stir for 2 hr. Concentrate the resulting suspension in vacuo and dry in a vacuum oven for 48 hr. Dissolve the residue in THF (25 mL) and cool in an ice bath for 30 min. Add 5 M aqueous sodium hydroxide (17.4 mL, 87.2 mmol) and 4-fluorobenzoyl chloride (3.78 mL, 40.4 mmol) dropwise. Warm the solution to room temperature and stir for one hour. Concentrate the black solution in vacuo and dilute with water (50 mL). Collect the solid by filtration and dry at 40° C. in a vacuum oven overnight to obtain the title compound (14.4 g, 91%). LC-ES/MS m/z 398 [M+H]$^+$.

PREPARATION 25 tert-Butyl 4-[(2S,3S)-3-[(4-fluorobenzoyl)amino]-2-hydroxy-indan-5-yl]-3-oxo-piperazine-1-carboxylate

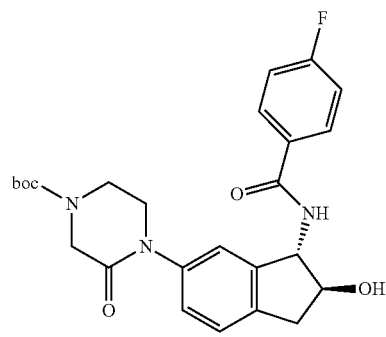

Purge a mixture of 4-fluoro-N-[(1S,2S)-2-hydroxy-6-iodo-indan-1-yl]benzamide (8.70 g, 21.9 mmol), 4-N-boc-2-oxo-piperazine (4.61 g, 22.3 mmol), and potassium carbonate (6.12 g, 43.8) in N-methylpyrrolidone (100 mL) with nitrogen gas. Add copper (I) iodide (2.11 g, 11.0 mmol) and sym-dimethylethylene diamine (2.34 mL, 21.9 mmol). Seal the flask with a septum and stir at 100° C. for 6 hr. Cool the mixture to room temperature and dilute with ethyl acetate (100 mL). Wash the organic portion with water (3×100 mL), then brine, and then dry over sodium sulfate, filter, and concentrate to dryness. Purify the residue by column chromatography (120 g silica, 2 to 5% methanol/chloroform) to obtain the title compound (7.63 g, 74%). LC-ES/MS m/z 470 [M+H]$^+$.

PREPARATION 26 tert-Butyl 4-[(3S,4S)-4-[(4-fluorobenzoyl)amino]-3-hydroxy-tetralin-6-yl]-3-oxo-piperazine-1-carboxylate

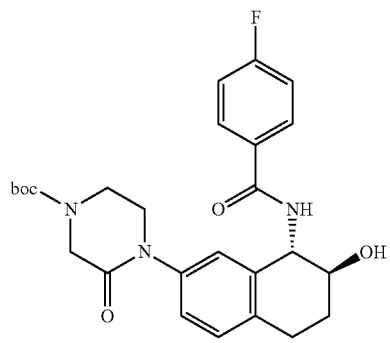

Prepare the title compound using N-[(1S,2S)-7-bromo-2-hydroxy-tetralin-1-yl]-4-fluoro-benzamide by essentially following Preparation 25 for tert-butyl 4-[(2S,3S)-3-[(4-fluorobenzoyl)amino]-2-hydroxy-indan-5-yl]-3-oxo-piperazine-1-carboxylate. LC-ES/MS m/z 484 [M+H]$^+$.

PREPARATION 27 tert-Butyl 4-[(2S,3S)-3-[(4-fluorobenzoyl)amino]-2-hydroxy-indan-5-yl]piperazine-1-carboxylate

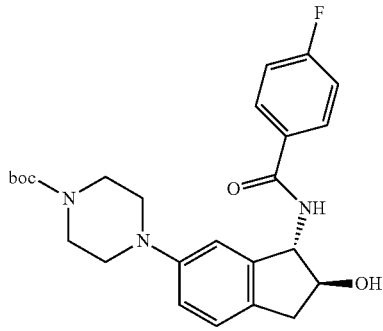

Cool a solution of tert-butyl 4-[(2S,3S)-3-[(4-fluorobenzoyl)amino]-2-hydroxy-indan-5-yl]-3-oxo-piperazine-1-carboxylate (8.85 g, 18.9 mmol) in anhydrous tetrahydrofuran (40 mL) in an ice bath for 30 min. and add borane-dimethyl sulfide complex (2 M, 37.7 mL, 75.40 mmol) under nitrogen. Warm the mixture to room temperature and stir for 1.5 hr. Add a second portion of borane-dimethyl sulfide complex (2 M, 9.42 mL, 18.9 mmol) at room temperature and stir for one hour. Cool in an ice bath for 10 min and carefully add water dropwise, followed by addition of saturated sodium bicarbonate solution (50 mL). Dilute the resulting suspension with ethyl acetate (150 mL). Wash the organic portion with brine, dry over sodium sulfate, and concentrate in vacuo. Purify the crude product by flash chromatography (120 g silica, 40 to 50% ethyl acetate/hexanes) to obtain the title compound (6.8 g, 79%). LC-ES/MS m/z 456 [M+H]+.

PREPARATION 28 tert-Butyl 4-[(3S,4S)-4-[(4-fluorobenzoyl)amino]-3-hydroxy-tetralin-6-yl]piperazine-1-carboxylate

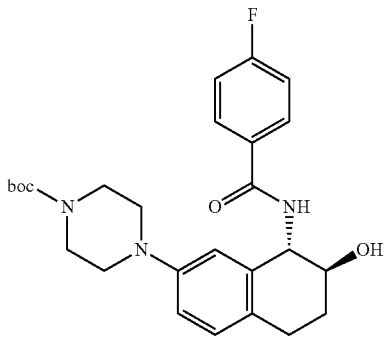

Prepare the title compound using tert-butyl 4-[(3S,4S)-4-[(4-fluorobenzoyl)amino]-3-hydroxy-tetralin-6-yl]-3-oxo-piperazine-1-carboxylate by essentially following Preparation 27 for tert-butyl 4-[(2S,3S)-3-[(4-fluorobenzoyl)amino]-2-hydroxy-indan-5-yl]piperazine-1-carboxylate. LC-ES/MS m/z 470 [M+H]+.

PREPARATION 29

4-Fluoro-N-[(1S,2S)-2-hydroxy-7-piperazin-1-yl-tetralin-1-yl]benzamide hydrochloride

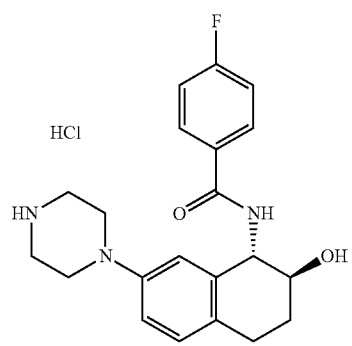

To a solution of tert-butyl 4-[(3S,4S)-4-[(4-fluorobenzoyl)amino]-3-hydroxy-tetralin-6-yl]piperazine-1-carboxylate (19.4 g, 41.3 mmol) in 1,4-dioxane (430 mL) add 4 M hydrogen chloride in dioxane (135 mL) at room temperature. Stir the resulting slurry mechanically at 50° C. for 13 hr. Concentrate the reaction in vacuo to obtain the title compound (24.8 g, quantitative). LC-ES/MS m/z 370 [M+H]+.

PREPARATION 30

4-Fluoro-N-[(3R,4S)-3-hydroxy-6-piperazin-1-yl-chroman-4-yl]benzamide hydrochloride

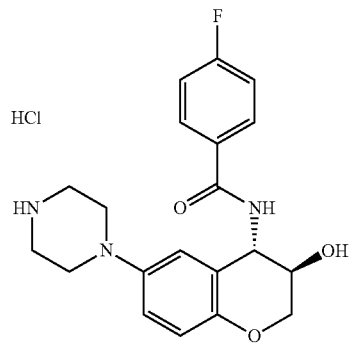

Degas (bubble nitrogen through the mixture) a suspension of tri-t-butylphosphonium tetrafluoroborate (16.0 g, 54.6 mmol) and allylpalladium(II) chloride dimer (5.07 g, 27.3 mmol) in DMSO (1.40 L) with stirring at room temperature. Add N-tert-butoxycarbonylpiperazine (315 g, 1.64 mol, 97% pure) and N-[(3R,4S)-6-bromo-3-hydroxy-chroman-4-yl]-4-fluoro-benzamide (200.0 g, 546 mmol). Stir the mixture for 15 min under nitrogen and then heat at 80° C. Add sodium tert-butoxide (179 g, 1.80 mol) and heat at 93-98° C. for 45 min. Pour the mixture over a solution of 1 M phosphoric acid (2.73 L, 2.73 mol, adjusted to pH=2.3 with 50% sodium hydroxide) and ethyl acetate (800 mL) and stir for 10 min. Separate the layers and extract the aqueous layer with ethyl acetate (3×300 mL). Wash the combined organic layer with semi-saturated brine (2×500 mL). Treat the organic layer with activated carbon (20 g) and silica gel (200 g) and stir for 30 min. Filter through a pad of diatomaceous earth and concentrate under reduced pressure to obtain a dark oil. Dissolve the oil in methanol (800 mL), add 4 M hydrogen chloride in dioxane (410 mL), and stir the solution at 40° C. for 1 hr. Evaporate the solvent in vacuo, suspend the residue in acetonitrile (1.6 L) and stir at room temperature for 1 hr. Collect the solid by filtration under nitrogen to avoid hydration of the salt. Wash the filtrate with acetonitrile (500 mL) and methyl tert-butyl ether (1 L), and dry under vacuum to obtain the title compound (262 g, 73%). LC-ES/MS m/z 372 [M+H]⁺.

Prepare the amines in the table below by essentially following the procedure described in Preparation 30 using the appropriate racemic or enantiopure bromide.

| Prep | Chemical name | Structure | LC-ES/MS m/z |
|---|---|---|---|
| 31 | Racemic-trans-4-fluoro-N-[6-hydroxy-3-piperazin-1-yl-6,7,8,9-tetrahydro-5H-benzo[7]annulen-5-yl]benzamide hydrochloride | 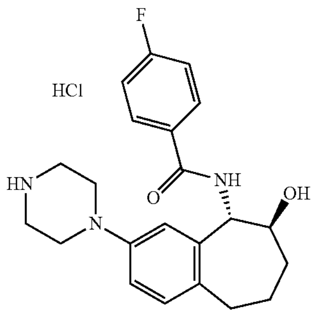 | 384 [M + H]⁺ |
| 32 | Racemic-trans-4-fluoro-N-[4-hydroxy-7-piperazin-1-yl-2,3,4,5-tetrahydro-1-benzoxepin-5-yl]benzamide hydrochloride | 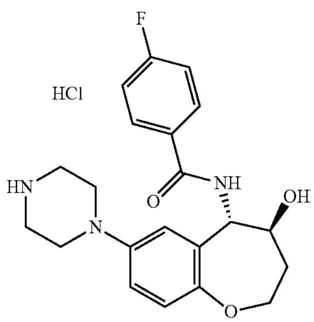 | 386 [M + H]⁺ |

PREPARATION 33

4-Fluoro-N-[(3R,4S)-3-hydroxy-6-[4-(oxetan-3-yl)piperazin-1-yl]chroman-4-yl]benzamide

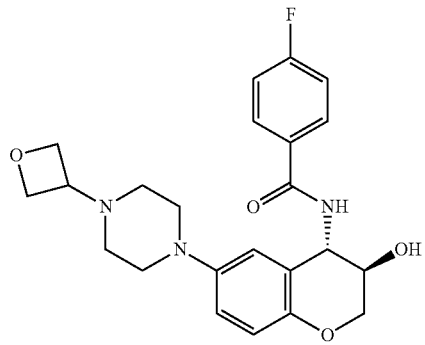

Add sodium triacetoxyborohydride (20 g, 94.4 mmol) to a slurry of 4-fluoro-N-[(3R,4S)-3-hydroxy-6-piperazin-1-yl-chroman-4-yl]benzamide hydrochloride (32.0 g, 78.5 mmol) and 3-oxetanone (6.87 g, 98.1 mmol) in acetonitrile (300 mL). Stir the slurry for 20 min. and add more sodium triacetoxyborohydride (20 g, 94.4 mmol) in one portion. Stir the brown mixture at 28° C. for approximately 2 hr. Add additional sodium triacetoxyborohydride (10 g, 47.2 mmol) and stir the mixture for 30 min. Add 3-oxetanone (2 g, 28.6 mmol) and after 20 min add additional 3-oxetanone (1 g, 14.3 mmol). Stir for 30 min., pour the mixture into a saturated aqueous sodium bicarbonate solution (1 L) and add dichloromethane (1 L). Separate the organic layer and concentrate in vacuo to obtain a pale grey solid. Purify the solid by silica gel column chromatography eluting with 3 to 6% isopropanol/dichloromethane to obtain the title compound as a white solid (19.2 g, 73%). LC-ES/MS m/z 428 [M+H]⁺.

Prepare the oxetanes in the table below by essentially following the procedure described in Preparation 33 using the appropriate racemic or enantiopure amine

| Prep | Chemical name | Structure | LC-ES/MS m/z |
|---|---|---|---|
| 34 | 4-Fluoro-N-[(1S,2S)-2-hydroxy-7-[4-(oxetan-3-yl)piperazin-1-yl]tetralin-1-yl]benzamide | 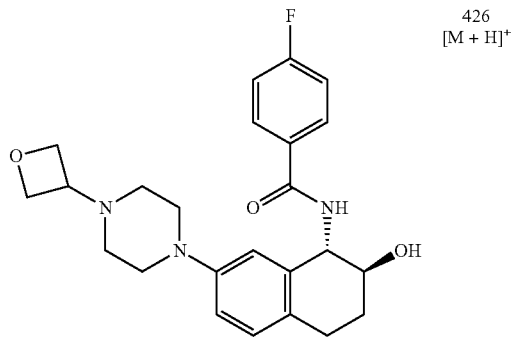 | 426 [M + H]⁺ |

| Prep | Chemical name | Structure | LC-ES/MS m/z |
|---|---|---|---|
| 35 | Racemic-trans-4-Fluoro-N-[8-hydroxy-2-[4-(oxetan-3-yl)piperazin-1-yl]-6,7,8,9-tetrahydro-5H-benzo[7]annulen-9-yl]benzamide | 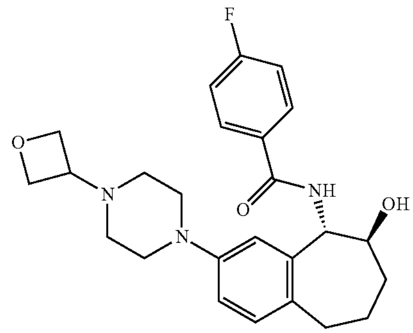 | 440 [M + H]+ |
| 36 | Racemic-trans-4-fluoro-N-[4-hydroxy-7-[4-(oxetan-3-yl)piperazin-1-yl]-2,3,4,5-tetrahydro-1-benzoxepin-5-yl]benzamide | 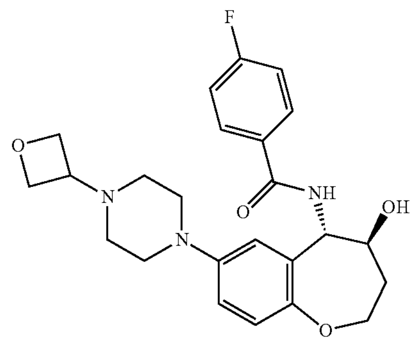 | 442 [M + H]+ |

PREPARATION 37

4-Fluoro-N-[(1S,2S)-2-hydroxy-6-[4-(oxetan-3-yl)piperazin-1-yl]indan-1-yl]benzamide

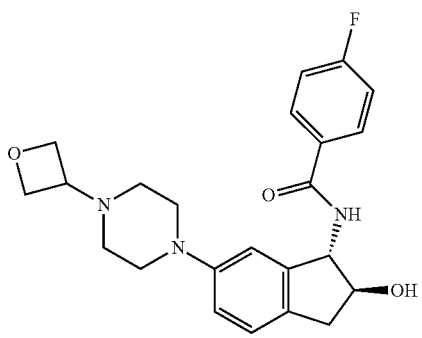

To a solution of tert-butyl 4-[(2S,3S)-3-[(4-fluorobenzoyl)amino]-2-hydroxy-indan-5-yl]piperazine-1-carboxylate (300 mg, 0.659 mmol) in 1,4-dioxane (5.0 mL), add 4 M hydrogen chloride in dioxane (5.0 mL) at room temperature and stir for 1 hr. Concentrate the suspension in vacuo. Add to the residue saturated aqueous sodium bicarbonate (50 mL) and extract with ethyl acetate (3×50 mL). Wash the combined organic layers with brine, dry over sodium sulfate, and concentrate in vacuo. Dissolve the residue in methanol (20 mL) and add 3-oxetanone (142 mg, 1.98 mmol), glacial acetic acid (170 µL, 2.96 mmol), and crushed activated 4 Å molecular sieves. Stir the resulting suspension at 50° C. for 1 hr. Add sodium cyanoborohydride (131 mg, 1.98 mmol) at room temperature and stir overnight. Add a saturated sodium bicarbonate solution (20 mL) and stir for 20 min. Extract with dichloromethane (3×50 mL) and wash the combined organic layers with water and brine. Dry the organic portion over sodium sulfate, filter, and concentrate to obtain the title compound (220 mg, 81%). LC-ES/MS m/z 412 [M+H]+.

PREPARATION 38

Racemic-trans-3,6-dibromochroman-4-ol

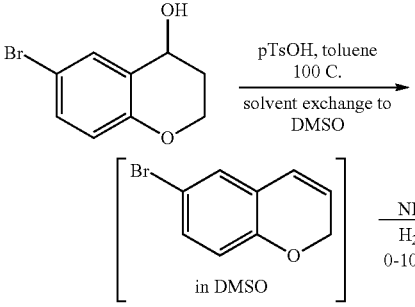

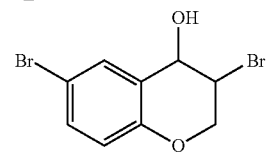

Heat a solution of 6-bromochroman-4-ol (25.0 g, 109.1 mmol) in toluene (500 mL) to 100° C. Add p-toluenesulfonic acid monohydrate (1.1 g, 5.5 mmol) and, using a Dean-Stark trap to collect water, stir at 100° C. for 2 hr. Remove the heat source and quench the reaction mixture with ice cold 0.5N NaOH (250 mL). Further cool the reaction mixture to 5-10° C., and then separate the layers. Wash the organic layer with water (25 mL) and concentrate the organics under reduced pressure to approximately half their original volume. Add DMSO (100 mL) and continue to concentrate under reduced pressure until no more toluene distills.

Cool the DMSO solution of the intermediate olefin to 0-5° C., add water (17 mL) and re-cool to 0-5° C. Add N-bromosuccinimide (21.7 g, 120.0 mmol) in 5 portions over 30 minutes. Stir at 0-5° C. for 1 hr. Dilute the reaction mixture with ethyl acetate (100 mL) and water (50 mL), stir 10 min., and separate the layers. Back extract the aqueous layer with ethyl acetate (100 mL). Wash the combined organics with 1:1 brine/water (2×50 mL), dry over sodium sulfate and concentrate under reduced pressure to obtain the title compound as a white solid (33.0 g, 99%). $^1$H NMR (DMSO-$d_6$) δ 4.26 (m, 1H), 4.37 (m, 2H), 4.65 (m, 1H), 6.27 (d, 1H), 6.80 (d, 1H), 7.35 (dd, 1H), 7.46 (bd, 1H). GC/MS m/z ($^{79}$Br/$^{81}$Br) 308/310 [M+].

PREPARATION 39

Racemic-trans-4-amino-6-bromo-chroman-3-ol

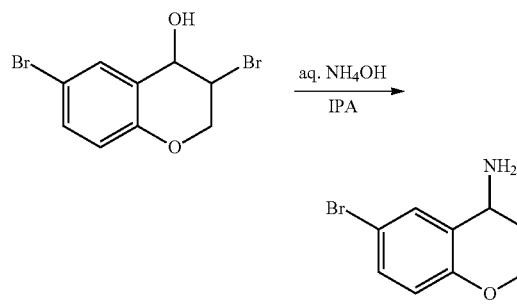

To a solution of racemic-trans-3,6-dibromochroman-4-ol (30.0 g, 97.4 mmol) in isopropyl alcohol (300 mL) at ambient temperature (500 mL), add ammonium hydroxide (28-30% aq., 150 mL, 2.2 mol). Stir slowly for 15 hr. Filter the reaction mixture and dilute the filtrate with water (200 mL). Concentrate the resulting solution under reduced pressure to one half of its original weight. Add water (100 mL), stir the mixture at ambient temperature for 10 min., then cool to 0-5° C. and stir for an additional 30 min. Collect the precipitate by filtration and wash the solids with water (25 mL) and heptanes (25 mL). Vacuum dry the material at 40° C. to afford the title compound as a pale yellow solid (21.2 g, 89.2%). $^1$H NMR (DMSO-$d_6$) δ 1.96 (bs, 2H), 3.53 (m, 2H), 3.87 (dd, 1H), 4.11 (dd, 1H), 5.15 (bs, 1H), 6.66 (d, 1H), 7.19 (dd, 1H), 7.48 (dd, 1H). LC-ES/MS m/z ($^{79}$Br) 244 [M+H].

PREPARATION 40

(3R,4S)-4-amino-6-bromo-chroman-3-ol

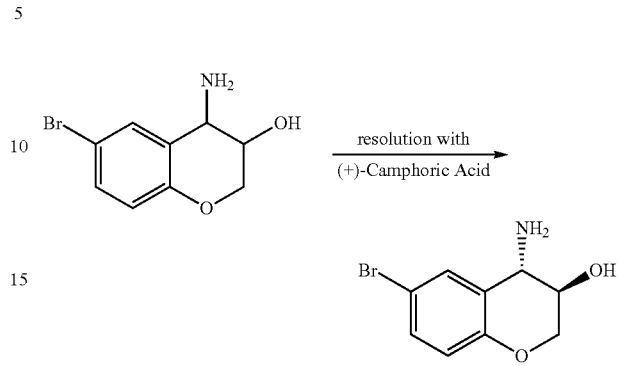

Heat a mixture of racemic-trans-4-amino-6-bromochroman-3-ol (21.1 g, 86.4 mmol), D-(+)-camphoric acid (17.3 g, 86.4 mmol), acetonitrile (633 mL) and water (47.6 mL) to 70-75° C. and stir for 10 min. The solution is allowed to cool to ambient temperature over 4 hr. After 24 hr. at ambient temperature, the mixture is filtered. Rinse the solids with 7% $H_2O$ in acetonitrile (2×20 mL). Heat the filtrate to 50° C. and add 1N NaOH (216.1 mL). Concentrate the resulting mixture under reduced pressure to remove the acetonitrile. Add $H_2O$ (211 mL) and heat the solution to 70° C. Cool to ambient temperature and collect the precipitate by filtration. Wash with water (25 mL) and vacuum dry at 50° C. overnight to obtain the title compound as an off-white solid (9.8 g, 46.4% of 50% theoretical weight, 98.7% ee).

Combine crude (3R,4S)-4-amino-6-bromochroman-3-ol (1.5 g, 6.15 mmol), acetonitrile (12.0 mL) and water (3.0 mL) and heat to 70-75° C. Stir the solution for 30 min. and allow the solution to cool to ambient temperature and then stir an additional 1 hr. Cool the mixture to 0-5° C. and stir 30 min. Filter the solids and wash with cold 4:1 acetonitrile: $H_2O$ (10 mL). Vacuum dry the solids at 50° C. overnight to obtain the purified title compound as a white solid (1.1 g, 74.6%, 99.7% ee). $^1$H NMR (DMSO-$d_6$) δ 1.96 (bs, 2H), 3.53 (m, 2H), 3.87 (dd, 1H), 4.11 (dd, 1H), 5.15 (bs, 1H), 6.66 (d, 1H), 7.19 (dd, 1H), 7.48 (dd, 1H). LC-ES/MS m/z ($^{79}$Br) 244 [M+H]. Conditions for analytical chiral HPLC analysis: ChiralPak AD-H column (150×4.6 mm, 4.6 micron); flow rate 0.6 mL/min; wavelength 290 nm; eluent 100% MeOH+0.2% v/v dimethyl-ethylamine; run time 10 min; column temperature 30° C.; isocratic.

PREPARATION 41

4-Fluoro-N-[(3R,4S)-3-hydroxy-6-(piperazin-1-yl) chroman-4-yl]benzamide

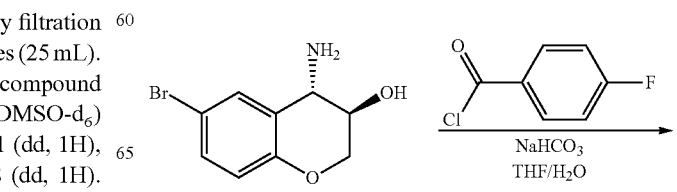

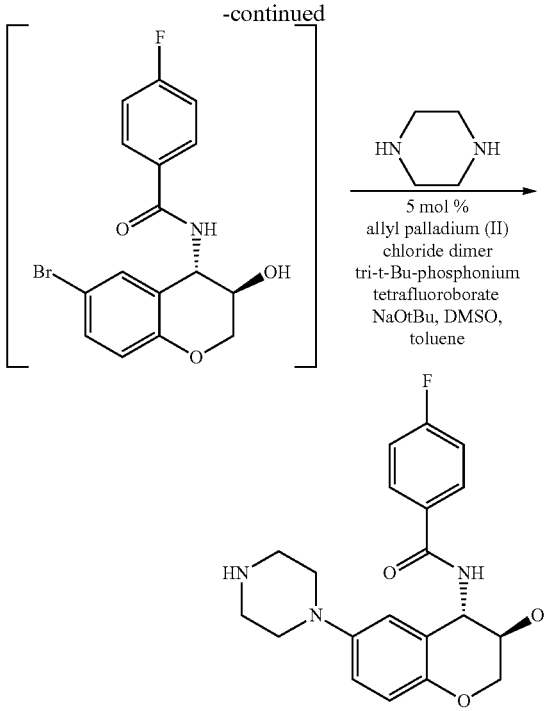

To a suspension of (3R,4S)-4-amino-6-bromo-chroman-3-ol (10.0 g, 41.0 mmol) in THF (50 mL) at ambient temperature, add sodium bicarbonate (5.2 g, 61.4 mmol) and water (50 mL). Stir 5 min. and cool the mixture to 0-5° C. Add 4-fluoro-benzoyl chloride (6.5 g, 41.0 mmol) drop-wise via an addition funnel over 10 min. Stir the mixture at 0-5° C. for 30 min., allow the mixture to warm to 15-20° C. and stir for an additional 2 hr. Dilute the mixture with brine (50 mL) and THF (50 mL) and stir for 20 min. Separate the layers and concentrate the organic layer to one half its original volume. Repeat the addition of THF (50 mL) and concentration to one half volume three times or until the Karl Fisher water analysis of the solution is <0.1%. Add DMSO (100 mL) and continue concentrating the mixture under reduced pressure at 50° C. until THF no longer distills.

Dilute the resulting DMSO solution of the amide intermediate with DMSO (200 mL) and toluene (45 mL) and de-gassed for 30 min. using a sub-surface sparge of nitrogen gas. Add piperazine (16.6 g, 192.7 mmol) and de-gas the solution for 30 min. Heat the solution to 40° C. and add allylpalladium (II) chloride dimer (0.72 g, 2 mmol) and tri-tert-butyl-phosphonium tetrafluoroborate (1.19 g, 4 mmol) under a nitrogen blanket. Stir the mixture 10 min and add sodium tert-butoxide (13.0 g, 135.3 mmol) under a nitrogen blanket. Raise the internal temperature to 70° C. and stir the mixture for 4 hr. Cool the reactor contents to 20° C. and add water (75 mL) over 15 min. Adjust the pH of the mixture to 6-7 using 6N HCl and add ethyl acetate (150 mL). Stir reactor contents for 30 min. and then separate the layers. Back extract the aqueous layer with ethyl acetate (2×150 mL). Discard the ethyl acetate extracts and adjust the pH of the aqueous layer to 11-12 using NaOH (40% aq.). Extract the aqueous layer with ethyl acetate (3×150 mL). Combine the organic extracts and concentrate under reduced pressure to approximately one half original volume. Add activated carbon (1.5 g) and heat the mixture to 50-55° C. Stir at 50-55° C. for 1 hr., cool the mixture to 20° C. and filter to remove solids. Wash the filtrate with brine (2×300 mL) and concentrate the organics under reduced pressure to approximately 2 volumes (based on original starting material). Cool the mixture to 0-5° C. and stir for an additional 3 hr. Isolate the solids by filtration, wash with methyl tert-butyl ether (30 mL) and vacuum dry the solids at 50° C. The title compound is recovered as an off-white solid (7.9 g, 52%). $^1$H NMR (DMSO-$d_6$) δ 2.40-2.80 (bm, 8H), 3.65-3.95 (bm, 2H), 4.13 (d, 1H), 4.95 (m, 1H), 5.35 (bs, 1H), 6.63 (dd, 1H), 6.69 (d, 1H), 6.80 (d, 1H), 7.27 (m, 2H), 7.96 (m, 2H), 8.72 (bd, 1H). LC-ES/MS m/z 372 [M+H].

PREPARATION 42

4-Fluoro-N-[(3R,4S)-3-hydroxy-6-[4-(oxetan-3-yl)piperazin-1-yl]chroman-4-yl]benzamide

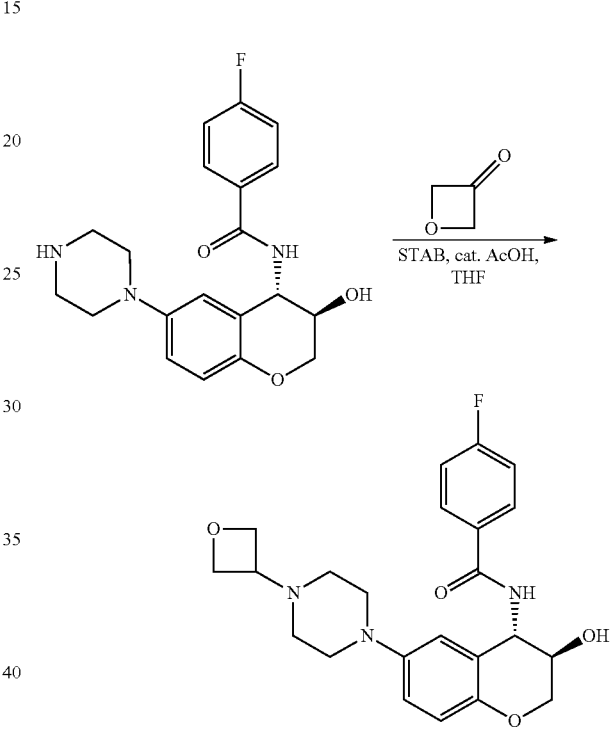

Combine 4-Fluoro-N-[(3R,4S)-3-hydroxy-6-(piperazin-1-yl)chroman-4-yl]benzamide (8.2 g, 22.0 mmol) and 3-oxetanone (2.4 g, 33.0 mmol) in THF (164 mL). Add acetic acid (1.3 mL, 22.0 mmol) and heat the resulting mixture to 35-40° C. After 1 hr., add sodium triacetoxyborohydride (8.4 g, 39.6 mmol) and stir at 35-40° C. for 4 hr. Cool the reaction mixture to 15° C. and add 2N NaOH (81.6 mL) over 30 min. Add brine (81.6 mL) and stir the mixture for 30 min. Separate the layers and dilute the organic layer with 2N NaOH (81.6 mL) and brine (81.6 mL). Stir the resulting mixture for 30 min. Separate the layers and remove the aqueous layer. To the organic layer, add activated carbon (1.0 g), raise the temperature to 50-55° C. and stir 1 hr. Filter the mixture to remove solids and concentrate the filtrate under reduced pressure to approximately one tenth of the original volume. Add ethyl acetate (164 mL) and concentrate under reduced pressure to approximately one fourth original volume. Repeat this process twice with ethyl acetate (2×164 mL). Concentrate the organics to approximately 3 volumes (based on starting material), raise the internal temperature to 70-75° C., and stir for 2 hr. Cool the mixture to 10° C., add heptane (82 mL) over 15 min and stir for an additional 2 hr. Isolate the technical grade title intermediate by filtration and vacuum dry the solids at 50-55° C. (10.1 g recovered).

Purification: Suspend technical grade 4-fluoro-N-[(3R,4S)-3-hydroxy-6-[4-(oxetan-3-yl)piperazin-1-yl]chroman-4-yl]benzamide (10.0 g, 23.4 mmol) in acetonitrile (700 mL) and heat the mixture to reflux. Stir at reflux for 2 hr., cool to 50-55° C. and add activated carbon (1.0 g). Stir at 50-55° C. for 2 hr. and filter to remove solids. Concentrate the filtrate under reduced pressure to approximately 5 volumes based on the starting technical grade material. Raise the internal temperature to 75-80° C. and stir for 1 hr. Cool the mixture to 20° C. and stir for an additional 4 hr. Isolate the title compound by filtration to afford a white solid (6.8 g, 72%). $^1$H NMR (DMSO-$d_6$) δ 2.33 (m, 4H), 2.94 (m, 4H), 3.40 (m, 1H), 3.85 (m, 1H), 3.93 (d, 1H), 4.14 (d, 1H), 4.40 (dd, 2H), 4.49 (dd, 2H), 4.94 (m, 1H), 5.34 (d, 1H), 6.65 (d, 1H), 6.70 (d, 1H), 6.84 (dd, 1H), 7.27 (m, 2H), 7.97 (m, 2H), 8.75 (bd, 1H). LC-ES/MS m/z 428 [M+H].

EXAMPLE 1

[(3R,4S)-4-[(4-Fluorobenzoyl)amino]-6-[4-(oxetan-3-yl)piperazin-1-yl]chroman-3-yl]N-methylcarbamate

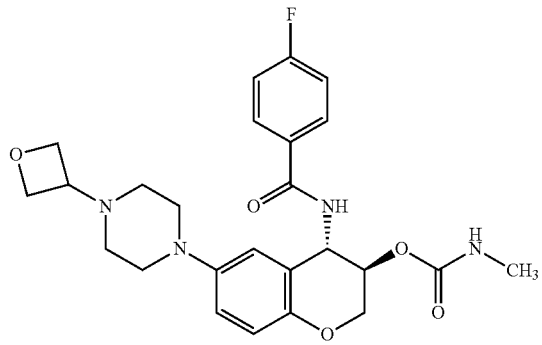

To a solution of 4-fluoro-N-[(3R,4S)-3-hydroxy-6-[4-(oxetan-3-yl)piperazin-1-yl]chroman-4-yl]benzamide (72.0 g, 168 mmol) in THF (648 mL) add 1,1'-carbonyldiimidazole (35.5 g, 219 mmol) and stir the solution at room temperature overnight. Cool the mixture to 5° C. and add a solution of 2 M methylamine in THF (210 mL, 421 mmol, 2.5 eq) dropwise over a period of 15 min. Stir for 30 min. and pour over a mixture of water (720 mL) and methyl tert-butyl ether (216 mL). Stir the mixture for 30 min. and decant the phases. Extract the aqueous phase with dichloromethane (3×216 mL). Wash the combined organic phases with brine (3×100 mL), dry over anhydrous sodium sulfate, and concentrate in vacuo. Suspend the residue in ethyl acetate (720 mL), heat at reflux for 2 hr. and cool to 10° C. Collect the solid by filtration and dry under vacuum overnight to obtain the title compound (64.0 g, 78%) as a white solid. LC-ES/MS m/z 485 [M+H]$^+$.

Prepare the carbamate in the table below by essentially following the procedure described in Example 1 using the appropriate enantiopure alcohol.

| Ex | Chemical name | Structure | LC-ES/MS m/z |
|---|---|---|---|
| 2 | [(1S,2S)-1-[(4-Fluorobenzoyl)amino]-7-[4-(oxetan-3-yl)piperazin-1-yl]tetralin-2-yl] N-methylcarbamate | 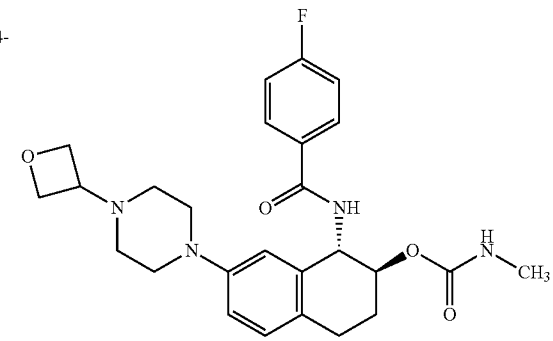 | 483 [M + H]$^+$ |

EXAMPLE 3

[(8S,9S)-9-[(4-Fluorobenzoyl)amino]-2-[4-(oxetan-3-yl)piperazin-1-yl]-6,7,8,9-tetrahydro-5H-benzo[7]annulen-8-yl]N-methylcarbamate

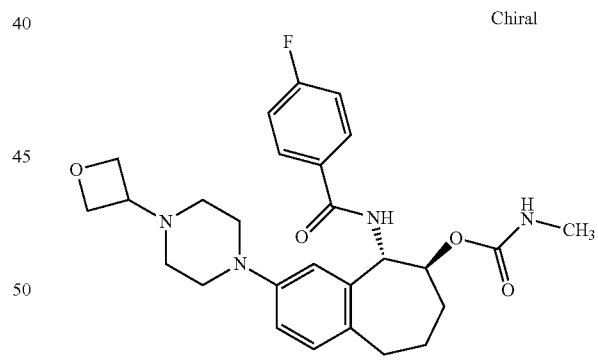

Prepare the racemic carbamate using racemic-trans-4-fluoro-N-[8-hydroxy-2-[4-(oxetan-3-yl)piperazin-1-yl]-6,7,8,9-tetrahydro-5H-benzo[7]annulen-9-yl]benzamide by essentially following the procedure for Example 1, above. LC-ES/MS m/z 497 [M+H]$^+$. Dissolve racemic-trans-9-[(4-fluorobenzoyl)amino]-2-[4-(oxetan-3-yl)piperazin-1-yl]-6,7,8,9-tetrahydro-5H-benzo[7]annulen-8-yl]N-methylcarbamate (1.03 g) in dichloromethane (8 mL) and methanol (3 mL). Separate the enantiomers in 300 μL portions by SFC on a CHIRALPAK® AD-H column (2.1×25 cm, 5 μm). Mobile phase: 30% isopropanol with 0.2% isopropylamine/carbon dioxide. Flow rate: 70 mL/min. Detection: 225 nm. Obtain the title compound as isomer 1 (333 mg, 99% ee) and the 8R,9R enantiomer as isomer 2 (359 mg, 97.5% ee). Determine enantiomeric excess by SFC on a CHIRALPAK® AD-H (4.6×150 mm, 5 μm) column using 30% isopropanol with 0.2% isopropylamine/carbon dioxide. Flow rate: 5 mL/min. Detection: 225 nm. Isomer 1 (title compound) $T_R$=1.76 min. Isomer 2 $T_R$=2.30 min.

EXAMPLE 4

[(4S,5S)-5-[(4-Fluorobenzoyl)amino]-7-[4-(oxetan-3-yl)piperazin-1-yl]-2,3,4,5-tetrahydro-1-benzoxepin-4-yl]N-methylcarbamate

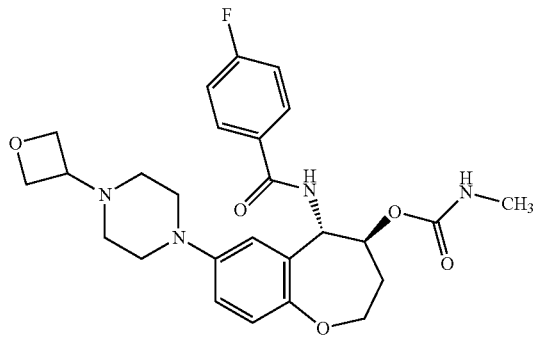

Prepare the racemic carbamate using racemic-trans-4-fluoro-N-[4-hydroxy-7-[4-(oxetan-3-yl)piperazin-1-yl]-2,3,4,5-tetrahydro-1-benzoxepin-5-yl]benzamide by essentially following the procedure for Example 1, above. LC-ES/MS m/z 499 [M+H]$^+$. Dissolve racemic-trans-[5-[(4-fluorobenzoyl)amino]-7-[4-(oxetan-3-yl)piperazin-1-yl]-2,3,4,5-tetrahydro-1-benzoxepin-4-yl]N-methylcarbamate (100 mg) in methanol (3 mL) and filter off insoluble solids. Separate the enantiomers in 1.5 mL portions (2 injections) by chromatography on a CHIRALPAK® AD-H column (3×25 cm, 5 μm). Mobile phase: 95% ethanol/5% acetonitrile. Flow rate: 18 mL/min. Detection: 225 nm. Obtain the title compound as isomer 1 (42 mg, 99% ee) and the 4R,5R enantiomer as isomer 2 (40 mg, 99% ee). Determine enantiomeric excess by HPLC on a CHIRALPAK® AD-H (4.6×150 mm, 5 μm) column using 95% ethanol/5% acetonitrile with 0.2% dimethylethylamine Flow rate: 1.0 mL/min. Detection: 225 nm. Isomer 1 (title compound) $T_R$=3.58 min. Isomer 2 $T_R$=5.13 min.

EXAMPLE 5

[(1S,2S)-1-[(4-Fluorobenzoyl)amino]-6-[4-(oxetan-3-yl)piperazin-1-yl]indan-2-yl]N-methylcarbamate

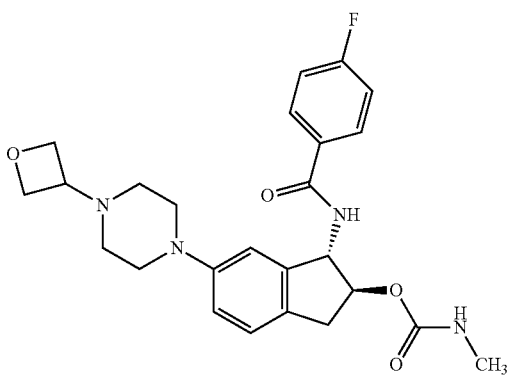

To a solution of 4-fluoro-N-[(1S,2S)-2-hydroxy-6-[4-(oxetan-3-yl)piperazin-1-yl]indan-1-yl]benzamide (220 mg, 0.535 mmol) in tetrahydrofuran (3.0 mL) add 4-pyrrolidinopyridine (16 mg, 0.107 mmol) and seal in a pressure vial. Add methyl isocyanate (97 μL, 1.60 mmol) by syringe to the mixture and stir at 60° C. overnight. Cool the resulting suspension in an ice bath, collect the white solid by filtration, and dry in a vacuum oven at 40° C. for 3 hr. to obtain the title compound (200 mg, 80%). LC-ES/MS m/z 469 [M+H]$^+$.

EXAMPLE 6

[(3R,4S)-4-[(4-Fluorobenzoyl)amino]-6-[4-(oxetan-3-yl)piperazin-1-yl]chroman-3-yl]N-methylcarbamate

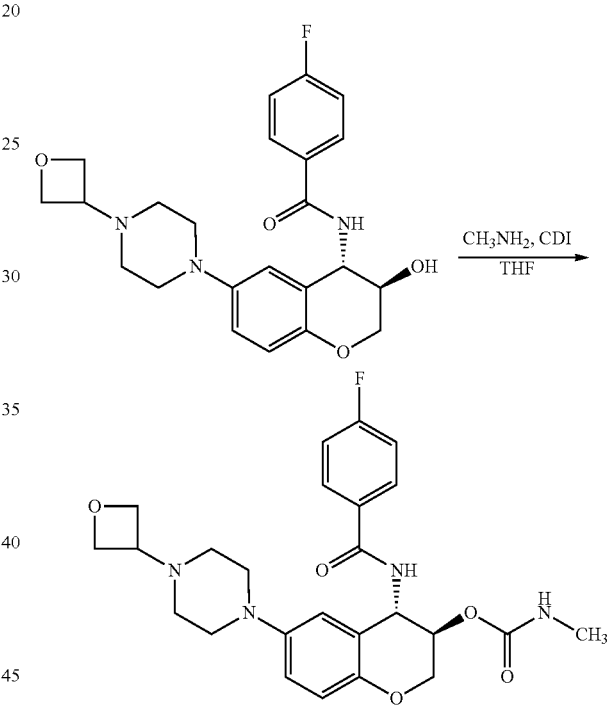

Suspend 4-fluoro-N-[(3R,4S)-3-hydroxy-6-[4-(oxetan-3-yl)piperazin-1-yl]chroman-4 yl]benzamide (10.0 g, 23.4 mmol) in THF (200 mL) and add 1,1 carbonyldiimidazole (4.9 g, 30.4 mmol). Stir at ambient temperature for 3 hr. Cool the reaction mixture to ⁻5° C. and add 2 M methyl amine (in THF, 21 mL, 42.1 mmol) over 15 min. Stir the resulting mixture at ⁻5-0° C. for 3 hr. Add 2 N NaOH (100 mL) and stir the mixture for 1 hr. at 10-30° C. Separate the layers and wash the organics with 2 N NaOH (4×100 mL). Add water (200 mL) and concentrate the mixture under reduced pressure to approximately twenty volumes (based on starting material). Add THF (200 mL) and stir at ambient temperature for 1 hr. Filter the mixture and transfer the product wetcake back to a clean reaction vessel. Add THF (200 mL) and water (200 mL) and stir at ambient temperature for 1 hr. Isolate the technical grade title compound by filtration and vacuum dry at 80° C. (9.0 g, 80%).

EXAMPLE 7

Crystallization/Solid Form Conversion of [(3R,4S)-4-[(4-Fluorobenzoyl)amino]-6-[4-(oxetan-3-yl)piperazin-1-yl]chroman-3-yl]N-methylcarbamate Suspend technical grade [(3R,4S)-4-[(4-fluorobenzoyl)amino]-6-[4-(oxetan-3-yl)piperazin-1-yl]chroman-3-yl]N-methylcarbamate (50 g, 103.2 mmol) in THF (1500 mL) under a nitrogen atmosphere. Heat the mixture to 50-60° C. and stir 1 hr. Add activated carbon (5.0 g) and continue stirring at 50-60° C. for 1 hr. Cool mixture to 40-50° C. and filter to remove solids. Concentrate the filtrate under reduced pressure to approximately 5 volumes (based on starting material). Add acetonitrile (1000 mL) and concentrate under reduced pressure to approximately 5 volumes. Repeat four times to remove all THF and then concentrate the mixture to 10-15 volumes. Heat the mixture to 70-75° C. and stir for 18 hr. Cool the mixture to 15° C. and stir 4 hr. Isolate the white crystals by filtration and vacuum dry at 55-60° C. to afford the title compound (42 g, 84%). $^1$H NMR (DMSO-$d_6$) δ 2.32 (m, 4H), 2.53 (d, 3H), 2.96 (m, 4H), 3.39 (m, 1H), 4.11-4.25 (m, 2H), 4.39 (dd, 2H), 4.51 (dd, 2H), 4.86 (m, 1H), 5.04 (m, 1H), 6.70-6.75 (m, 2H), 6.85 (dd, 1H), 7.17 (m, 1H) 7.28 (m, 2H), 7.96 (m, 2H), 8.90 (bd, 1H). LC-ES/MS m/z 485 [M+H]. Chiral assay 99.9% ee.

Exemplified compounds of the present invention are tested in the following in vitro and in vivo assays.

In vitro

Potency assays for human cathepsin S and mouse cathepsin S and selectivity assays for human cathepsins L, B, K, V, and F are described below. The experimental conditions and/or materials of each assay differ slightly and therefore such differences are noted either directly within the general assay conditions or coded according to the respective enzyme assay using designations 1a through 1 g in Table 1 immediately following the general assay conditions.

Test compounds are prepared in DMSO to make up a 10 mM stock solution. The stock solution is serially diluted in DMSO to obtain a ten-point dilution curve with a final compound concentration range 1a in a 96-well round-bottom plate before conducting the in vitro enzymatic assay. Compounds are further diluted 1b in assay buffer (used for entire assay) described immediately hereafter:

Human cathepsins S, L, B, F and mouse cathepsin S: 50 mM sodium phosphate (pH 6.5) containing 2.5 mM DTT and 2.5 mM EDTA plus 0.01% TRITON® X-100

Human cathepsins K and V: 100 mM sodium acetate (pH 5.5) containing 100 mM NaCl, 2.5 mM DTT and 2.5 mM EDTA plus 0.01% TRITON® X-100

Ten μL of each dilution is added to each well of row A through H of a corresponding low protein binding half area black plate (Costar 3694). Amount 1c of substrate, benzyloxycarbonyl-L-leucyl-L-arginine-4-methyl-coumaryl-7-amide (Peptide Institute), prepared in assay buffer, is added to each well of the plate for a final concentration 1d. Amount 1e of the respective enzyme, described immediately hereafter, prepared in assay buffer is added to each well of the plate containing substrate and test compound resulting in a final concentration 1f to initiate the reaction.

Human cathepsins S, L, K, and V: Obtained from Calbiochem.

Mouse cathepsin S: Briefly, mouse cathepsin S is cloned in baculovirus using a mCathepsin S-pAN51(T760) construct containing a histidine tag. IMAC is then employed to purify the active protein.

Human cathepsin F: Briefly, human recombinant cathepsin F enzyme is prepared in house as follows. Procathepsin F is cloned in 293 E cells using the CathepsinF-pAN60 (T-2188) construct containing a histidine tag. IMAC is then employed to purify the protein. The procathepsin F is digested using pepsin and repurified using Mono S column chromatography resulting in purified activated cathepsin F.

The mixture is briefly shaken at low speed on a plate mixer. The RFU of the mixture is recorded using an Envision 2103 Multilabel Reader at excitation wavelength 355 nm and emission wavelength 460 nm for 0.1 sec after an incubation time 1 g at room temperature. RFU are plotted versus inhibitor concentration and a curve is fitted with a four-parameter logistic equation to obtain $IC_{50}$ values using Activity Base (ver. 7.3.2.1). For Human cathepsin F, a Packard Fusion Alpha Microplate Reader (0.5 sec reading/well) is used to measure RFU and GraphPad Prism 4.03 software is used to plot RFU versus inhibitor concentration.

TABLE 1

In vitro assay experimental conditions

| | Cathepsins | | | | | | |
|---|---|---|---|---|---|---|---|
| Conditions | Human S | Mouse S | Human L | Human B | Human K | Human V | Human F |
| 1a | 166 μM to 50 pM | 166 μM to 50 pM | 166 μM to 50 pM | 166 μM to 50 pM | 166 μM to 50 pM | 166 μM to 50 pM | 900 μM to 45 nM |
| 1b | 20X | 20X | 20X | 20X | 20X | 20X | 10X |
| 1c | 10 μL | 10 μL | 10 μL | 25 μL | 25 μL | 25 μL | 10 μL |
| 1d | 25 μM | 25 μM | 20 μM | 37.5 μM | 35 μM | 35 μM | 25 μM |
| 1e | 10 μL | 10 μL | 10 μL | 15 μL | 15 μL | 15 μL | 10 μL |
| 1f | 150 μM | 2700 μM | 20 μM | 100 μM | 67 μM | 439 μM | 87 ng/ml |
| 1g | 1 h | 1 h | 1 h | 1 h | 2 h | 1 h | 1 h |

Following a protocol essentially as described above, exemplified compounds display $IC_{50}$s in the human cathepsin S and mouse cathepsin S enzyme inhibitor assay of less than 800 nM and 400 nM, respectively. Particularly, the compounds of Examples 1 and 2 display $IC_{50}$s in the human cathepsin S enzyme inhibitor assay of about 6.4 nM and 10.2 nM respectively, and in the mouse cathepsin S enzyme inhibitor assay of about 1.7 nM and 3.9 nM, respectively, thus demonstrating that certain compounds within the scope of the present invention are potent inhibitors of human and mouse cathepsin S.

For human cathepsins L, B, K, and V enzyme inhibitor assays, the compound of Example 1 displayed $IC_{50}$s of about >167 μM, 5.2 μM, >100 μM, and 33 μM, respectively, and Example 2 of about >167 μM, 94 μM, >100 μM, and >100 μM, respectively. For human cathepsin F, the compound of Example 1 displays no inhibition up to 30 µM. These results demonstrate that certain compounds within the scope of the present invention are selective inhibitors of cathepsin S.

In vivo

CaCl$_2$-induced AAA Animal Efficacy Model

The AAA animal efficacy model using CaCl$_2$ induction to study the effect of cathepsin S inhibitors on AAA (*J. Clin. Invest.*, 2002, 110(5), 625-632) is modified as described below.

Wild-type male 129SvEv mice (10 weeks old) from Taconic (Cambridge City, Ind.) divided into six groups for Example 1 and five groups for Example 2 with each group containing 12 mice are used. Groups 1-5 for Examples 1 and 2 are administered respectively a vehicle solution 1% NATROSOL® (hydroxyethylcellulose)/0.25% TWEEN® 80 (polysorbate 80)/0.05% Antifoam-15100 (Dow Corning) and 1, 3, 10, or 30 mg/kg of test compound in vehicle solution, by oral gavage b.i.d. for 4 weeks. Group 6 (in the study of Example 1) representing a sham group (0.9% saline applied to the aorta instead of CaCl$_2$ and dosed with vehicle) is included to establish a baseline. The first dose is given one day prior to surgery (p.m.) and the second dose is given the morning of surgery. Animals do not receive a p.m. dose on the day of surgery. B.i.d. dosing (a.m. and p.m.) is continued the day after surgery for 28 days.

On the day of surgery, animals received analgesia (BU-PRENEX®, 0.1 mg/kg) subcutaneously 10 min. pre-operatively and 3 hr. post-operatively. Mice are anesthetized by inhalation of 2% isoflurane and a laparotomy is performed. The abdominal aorta is exposed by retracting the bowel laterally with a surgical retractor and leaving the bowel in the abdominal cavity. The abdominal aorta from the level of the renal arteries to the iliac bifurcation is isolated from the inferior vena cava and surrounding connective tissues using micro-surgical techniques. Once isolated, the region of interest of the abdominal aorta is wrapped with a premeasured sterile cotton gauze soaked in 0.25 M aqueous CaCl$_2$ solution. In sham control animals, 0.9% saline is substituted for CaCl$_2$. After 7 min., the gauze is removed and a second CaCl$_2$ soaked gauze (or 0.9% saline soaked gauze in sham animals) is applied. Following a second 7 minute period, the gauze is removed, the aorta is rinsed with 0.9% saline and the abdomen is closed. The animals are returned to general housing where they are housed individually with ad lib access to standard rodent diet (Purina 2014) and water.

After 4 weeks of dosing as described above, the aortic luminal perimeter, area and diameter of the aortic segments that were wrapped with gauze are determined by ultrasound (Biosound Ultrasound—7.5 MHz) and statistically analyzed with JMP® 7 software (Cary, N.C.). Percentage reductions of AAA determined by measurement of the aortic luminal perimeter (which represents in this instance a more accurate measurement of the abdominal aorta due to the irregular geometry associated with the aortic segment being measured) are shown below in Table 1 and are represented as means±standard deviation. For Example 1, vehicle group is compared to sham group, and testing compound is compared to vehicle. For Example 2, testing compound is compared to vehicle.

TABLE 2

In Vivo Percentage (%) Reduction of AAA

| Group | Example 1 | Example 2 |
|---|---|---|
| Vehicle | 0 ± 9 | 0 ± 8 |
| 1 mg/kg | 58 ± 10 | 11 ± 7 |
| 3 mg/kg | 83 ± 8 | 32 ± 9 |
| 10 mg/kg | 87 ± 8 | 43 ± 9 |
| 30 mg/kg | 87 ± 7 | 52 ± 7 |

Following a protocol essentially as described above, the compounds of Examples 1 and 2 reduce the aortic luminal perimeter in a dose-dependent manner, and therefore demonstrate that certain compounds within the scope of the invention reduce AAA.

p10 Accumulation Assay

Wild-type male C57B6 or 129SvEv mice (10 weeks old) from Taconic (Cambridge City, Ind.) divided into four groups are used, with each group having 3 mice. Groups 1-4 are administered respectively a vehicle solution 1% NATROSOL® (hydroxyethylcellulose)/0.25% TWEEN® 80 (polysorbate 80)/0.05% Antifoam-1510 (Dow Corning) and 3, 10, or 30 mg/kg of test compound in vehicle solution by oral gavage. After 4 hr., whole blood (300-500 µL) is drawn from each mouse. The step of removing red blood cells is performed by adding one mL Flow Cytometry Lysing Solution™ (Santa Cruz Biotechnology, Inc.), keeping at room temperature for 10 min., centrifuging at 4000 rpm for 5 min. and then discarding the supernatant. This step is repeated once to remove the red blood cells completely. The PWBC pellet is resuspended with 50 µL CytoBuster™ Reagent (Novagen) and sonicated at high power for 5-10 sec. The protein concentrations are determined using a BCA assay (*Anal. Biochem.* 1988, 175, 231-237).

The p10 amount is determined using a Western blot. Samples (0.5 µg/µl protein concentration) are denatured at 96° C. for 5 min. and 20 µl/well of samples (10 µg/well) are loaded to 4-12% NUPAGE® NOVEX® Bis-Tris Midi-gel (Invitrogen). Gels are run at 120 V for 60 min. with the NUPAGE® MES SDS running buffer (Invitrogen). Proteins are transferred to 0.2 µm nitrocellulose (BIO-RAD) at 100 V for 30 min. with NUPAGE® Transfer Buffer (Invitrogen) and 20% methanol (EMD). Blot is briefly rinsed with PBS and blocked in 10 mL in ODYSSEY® Blocking Buffer (LI-COR Biosciences) at room temperature for 60 min. For p10, the blot is incubated with primary antibody against mouse CD74 (1 µg/ml of rat anti-CD74 antibody)(BD Bioscience) in blocking buffer at 4° C. overnight. For tubulin control, the blot is incubated with rabbit anti-beta tubulin pAb (0.2 µg/ml) (Abcam) in blocking buffer at 4° C. overnight. The blot is washed with washing buffer (DPBS from HyClone) with 0.01% polysorbate 20 four times for 10 min. each. The blot is then incubated with secondary antibody at room temperature for 60 min. For p10, ALEXA FLUOR® 680 goat anti rat IgG (1:5000 dilution)(Invitrogen) is used. For tubulin, ALEXA FLUOR® 680 goat anti rabbit IgG (1:5000 dilution)(Invitrogen). The blot is again washed as described above and placed in PBS for scanning.

The images are captured by scanning on an ODYSSEY® Infrared Imager (LI-COR Biosciences). The p10 amount is analyzed with ODYSSEY® software and normalized with the tubulin amount. The data are statistically analyzed with JMP® 7 software (Cary, N.C.). Relative p10 accumulations (fold increase) to the vehicle are shown in Table 3. Values are represented as means±standard deviation.

TABLE 3

In vivo relative p10 accumulation in PWBC

| Group | Example 1 | Example 2 |
|---|---|---|
| Vehicle | 1.0 ± 0.8 | 1.0 ± 0.2 |
| 3 mg/kg | 2.1 ± 0.5 | 1.1 ± 0.7 |
| 10 mg/kg | 3.9 ± 0.2 | 2.2 ± 1.3 |
| 30 mg/kg | 4.6 ± 1.0 | 4.6 ± 1.2 |

Following the above protocol, the compounds of Examples 1 and 2 dose dependently increase p10 in PWBC, demonstrating that certain compounds within the scope of the invention block antigen presentation.

We claim:

1. A compound of the formula

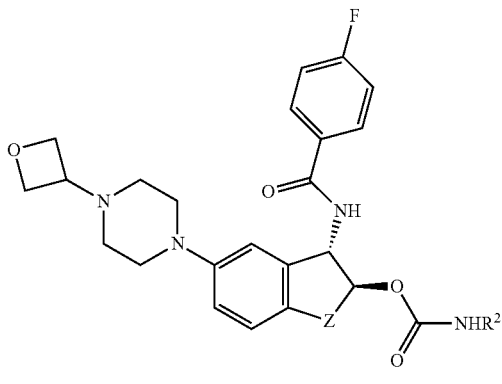

wherein,

Z is —CH$_2$—, —CH$_2$CH$_2$—, —OCH$_2$—, —CH$_2$CH$_2$CH$_2$—, or —OCH$_2$CH$_2$—;

R$^1$ is H, F, or Cl;

R$^2$ is H, methyl, ethyl, propyl, or isopropyl;

or a pharmaceutically acceptable salt thereof.

2. The compound according to claim 1, wherein R$_1$ is H or F, or a pharmaceutically acceptable salt thereof.

3. The compound according to claim 1, wherein R$_1$ is F, or a pharmaceutically acceptable salt thereof.

4. The compound according to claim 1, wherein R$_2$ is methyl or ethyl, or a pharmaceutically acceptable salt thereof.

5. The compound according to 1, wherein R$_2$ is methyl, or a pharmaceutically acceptable salt thereof.

6. The compound according to claim 3, wherein R$_2$ is methyl, or a pharmaceutically acceptable salt thereof.

7. The compound according to 1, wherein Z is —CH$_2$CH$_2$— or —OCH$_2$—, or a pharmaceutically acceptable salt thereof.

8. The compound according to claim 1, having the formula:

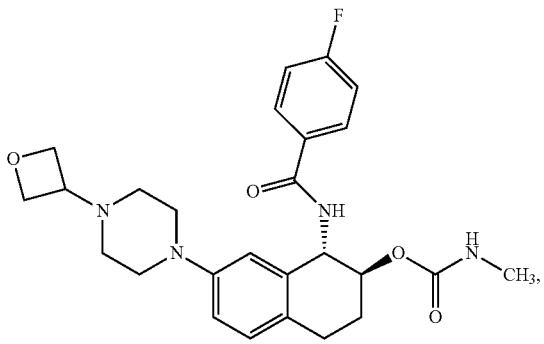

or a pharmaceutically acceptable salt thereof.

9. The compound according to claim 1, having the formula:

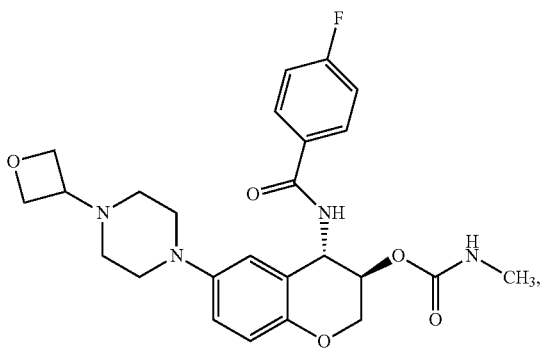

or a pharmaceutically acceptable salt thereof.

10. The compound according to claim 1, having the formula:

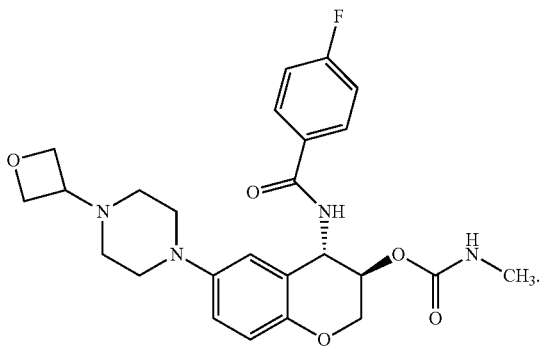

11. A pharmaceutical composition comprising a compound of the formula

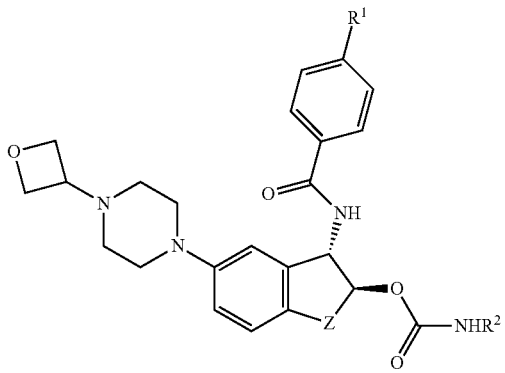

wherein,
Z is —CH₂—, —CH₂CH₂—, —OCH₂—, —CH₂CH₂CH₂—, or —OCH₂CH₂—;
R¹ is H, F, or Cl;
R² is H, methyl, ethyl, propyl, or isopropyl;
or a pharmaceutically acceptable salt thereof, and a pharmaceutically acceptable diluent or carrier.

12. The pharmaceutical composition of claim 11 wherein the compound is [(1S,2S)-1-[(4-Fluorobenzoyl)amino]-7-[4-(oxetan-3-yl)piperazin-1-yl]tetralin-2-yl]N-methylcarbamate, or a pharmaceutically acceptable salt thereof.

13. The pharmaceutical composition of claim 11 wherein the compound is [(3R,4S)-4-[(4-Fluorobenzoyl)amino]-6-[4-(oxetan-3-yl)piperazin-1-yl]chroman-3-yl]N-methylcarbamate, or a pharmaceutically acceptable salt thereof.

14. The pharmaceutical composition of claim 11 wherein the compound is [(3R,4S)-4-[(4-Fluorobenzoyl)amino]-6-[4-(oxetan-3-yl)piperazin-1-yl]chroman-3-yl]N-methylcarbamate.

15. A method for the treatment of abdominal aortic aneurysm, plaque instability, atherosclerosis, or rheumatoid arthritis in a mammal in need thereof, comprising administering to said mammal a therapeutically effective amount of a compound of the formula

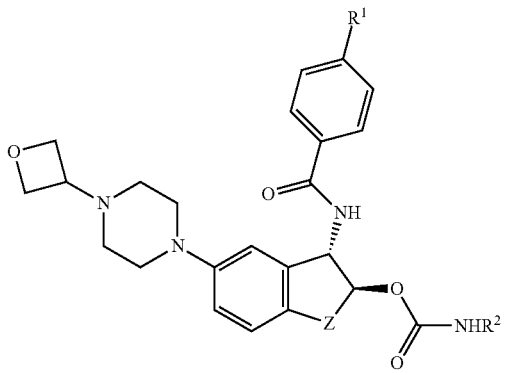

wherein,
Z is —CH₂—, —CH₂CH₂—, —OCH₂—, —CH₂CH₂CH₂—, or —OCH₂CH₂—;
R¹ is H, F, or Cl;
R² is H, methyl, ethyl, propyl, or isopropyl;
or a pharmaceutically acceptable salt thereof.

16. The method of claim 15 wherein the compound is of the formula:

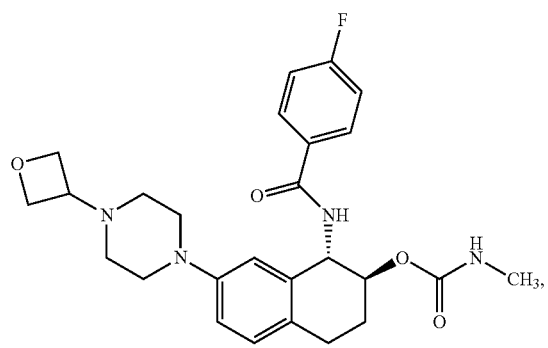

or a pharmaceutically acceptable salt thereof.

17. The method of claim 15 wherein the compound is of the formula:

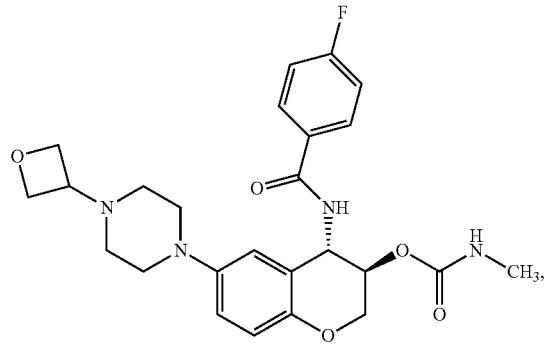

or a pharmaceutically acceptable salt thereof.

18. The method according to claim 15, wherein said mammal is a human.

19. The method according to claim 16, wherein said mammal is a human.

20. The method according to claim 17, wherein said mammal is a human.

* * * * *

UNITED STATES PATENT AND TRADEMARK OFFICE
CERTIFICATE OF CORRECTION

PATENT NO. : 8,227,468 B2
APPLICATION NO. : 13/273302
DATED : July 24, 2012
INVENTOR(S) : Gary G. Deng et al.

It is certified that error appears in the above-identified patent and that said Letters Patent is hereby corrected as shown below:

In the issued patent, please note the following corrections:

Cover Page, Item (75) Column 1, Line 4, Delete "Zioinsville, IN" and insert -- Zionsville, IN --, Column 39, Line 26-44 (approx.)

In Claim 1, delete " 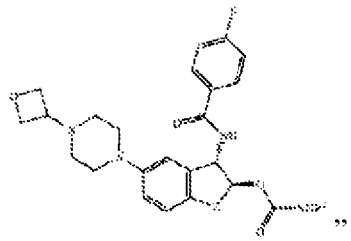 "

and insert -- 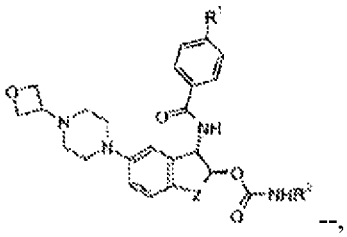 --,

Column 39, Line 60, In Claim 5, delete "to" and insert -- to claim --,

Column 39, Line 62, In Claim 6, delete "to" and insert -- to claim --,

Column 39, Line 64, In Claim 7, delete "to" and insert -- to claim --,

Signed and Sealed this
Sixteenth Day of October, 2012

David J. Kappos
*Director of the United States Patent and Trademark Office*